United States Patent
Tsuboi

(10) Patent No.: US 11,282,877 B2
(45) Date of Patent: Mar. 22, 2022

(54) PHOTOELECTRIC CONVERSION APPARATUS AND PHOTOELECTRIC CONVERSION SYSTEM

(71) Applicant: CANON KABUSHIKI KAISHA, Tokyo (JP)

(72) Inventor: Hiromasa Tsuboi, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/950,746

(22) Filed: Nov. 17, 2020

(65) Prior Publication Data
US 2021/0159256 A1 May 27, 2021

(30) Foreign Application Priority Data
Nov. 27, 2019 (JP) .............................. JP2019-214781

(51) Int. Cl.
*G01T 1/20* (2006.01)
*H01L 27/146* (2006.01)
(Continued)

(52) U.S. Cl.
CPC .......... *H01L 27/1461* (2013.01); *A61B 6/037* (2013.01); *G01S 17/10* (2013.01);
(Continued)

(58) Field of Classification Search
CPC ........... H01L 27/1461; H01L 27/14621; H01L 27/14627; H01L 27/14634; H01L 27/14636; H01L 27/1464; H01L 27/14663; H01L 27/14645; H01L 31/107; H01L 27/14612; H01L 27/14603; G01S 17/10; G01S 17/931; G01T 1/2018; G01T 1/24; A61B 6/037
See application file for complete search history.

(56) References Cited

U.S. PATENT DOCUMENTS

2020/0058821 A1    2/2020    Baba

FOREIGN PATENT DOCUMENTS

| EP | 3555919 A1 | 10/2019 | |
| JP | 2006108514 A * | 4/2006 | ......... H01L 29/7835 |

(Continued)

*Primary Examiner* — Kiho Kim
(74) *Attorney, Agent, or Firm* — Canon U.S.A., Inc. IP Division

(57) ABSTRACT

A photoelectric conversion apparatus includes a semiconductor substrate, a first semiconductor region of a first conductivity type, a second semiconductor region of a second conductivity type, an embedded electrode, and an insulation member arranged between the embedded electrode and the first semiconductor region and the second semiconductor region. A deepest portion of the embedded electrode is arranged at a position deeper than a p-n junction surface of the first semiconductor region and the second semiconductor region. A potential difference between the first semiconductor region and the second semiconductor region is a potential difference at which avalanche multiplication does not occur, and a potential difference between the embedded electrode and the second semiconductor region is a potential difference at which avalanche multiplication occurs.

29 Claims, 16 Drawing Sheets

(51) Int. Cl.
*G01S 17/10* (2020.01)
*G01S 17/931* (2020.01)
*G01T 1/24* (2006.01)
*A61B 6/03* (2006.01)
*H01L 31/107* (2006.01)

(52) U.S. Cl.
CPC .......... *G01S 17/931* (2020.01); *G01T 1/2018* (2013.01); *G01T 1/24* (2013.01); *H01L 27/1464* (2013.01); *H01L 27/14621* (2013.01); *H01L 27/14627* (2013.01); *H01L 27/14634* (2013.01); *H01L 27/14636* (2013.01); *H01L 27/14645* (2013.01); *H01L 27/14663* (2013.01); *H01L 31/107* (2013.01)

(56) References Cited

FOREIGN PATENT DOCUMENTS

| | | |
|---|---|---|
| JP | 2018019040 A | 2/2018 |
| JP | 2019197833 A | 11/2019 |

\* cited by examiner

PHOTOELECTRIC CONVERSION APPARATUS AND PHOTOELECTRIC CONVERSION SYSTEM

BACKGROUND

Field

One disclosed aspect of the embodiments relates to a photoelectric conversion apparatus and a photoelectric conversion system.

Description of the Related Art

A photoelectric conversion apparatus using an avalanche diode that detects a signal by avalanche multiplication is known. Japanese Patent Application Laid-Open No. 2018-19040 discusses a technique that reduces the time required to detect charge generated in a deep portion of a semiconductor substrate using an embedded electrode.

A photoelectric conversion apparatus discussed in Japanese Patent Application Laid-Open No. 2018-19040 uses an avalanche diode, and an electric field that is strong enough to cause avalanche multiplication is generated between a p-n junction of the avalanche diode. In order to generate such a strong electric field, the photoelectric conversion apparatus discussed in Japanese Patent Application Laid-Open No. 2018-19040 requires a great potential difference between a potential applied to an anode of the avalanche diode and a potential applied to a cathode of the avalanche diode. Since an avalanche current flows between the p-n junction, the photoelectric conversion apparatus discussed in Japanese Patent Application Laid-Open No. 2018-19040 has a high power consumption.

SUMMARY

According to an aspect of the present disclosure, a photoelectric conversion apparatus includes a semiconductor substrate, a first semiconductor region of a first conductivity type in the semiconductor substrate, a second semiconductor region of a second conductivity type in the semiconductor substrate, an embedded electrode, and an insulation member. The semiconductor substrate includes a first surface and a second surface facing the first surface. The first conductivity type uses, as a majority carrier, a same carrier as a signal carrier. The embedded electrode is arranged in the semiconductor substrate in a depth direction from the first surface toward the second surface. The insulation member is arranged between the embedded electrode and the second semiconductor region and the first semiconductor region. A deepest portion of the embedded electrode is at a position deeper than a p-n junction surface of the first semiconductor region and the second semiconductor region. A potential difference between the first semiconductor region and the second semiconductor region is a potential difference at which avalanche multiplication does not occur between the first semiconductor region and the second semiconductor region. A potential difference between the embedded electrode and the second semiconductor region is a potential difference at which avalanche multiplication occurs between the embedded electrode and the second semiconductor region.

According to another aspect of the present disclosure, A photoelectric conversion apparatus includes a semiconductor substrate, a first semiconductor region of a first conductivity type arranged in the semiconductor substrate, a second semiconductor region of a second conductivity type arranged in the semiconductor substrate, an embedded electrode, and an insulation member. The semiconductor substrate includes a first surface and a second surface facing the first surface. The first conductivity type uses, as a majority carrier, a same carrier as a signal carrier. The embedded electrode is arranged in the semiconductor substrate in a depth direction from the first surface toward the second surface. The insulation member is arranged between the second semiconductor region and the embedded electrode An avalanche multiplication region is formed between the embedded electrode and the second semiconductor region. The avalanche multiplication region is in contact with the first semiconductor region. A potential difference between the first semiconductor region and the second semiconductor region is a potential difference at which avalanche multiplication does not occur between the first semiconductor region and the second semiconductor region.

Further features of the present disclosure will become apparent from the following description of exemplary embodiments with reference to the attached drawings.

DESCRIPTION OF THE EMBODIMENTS

Figure 1:
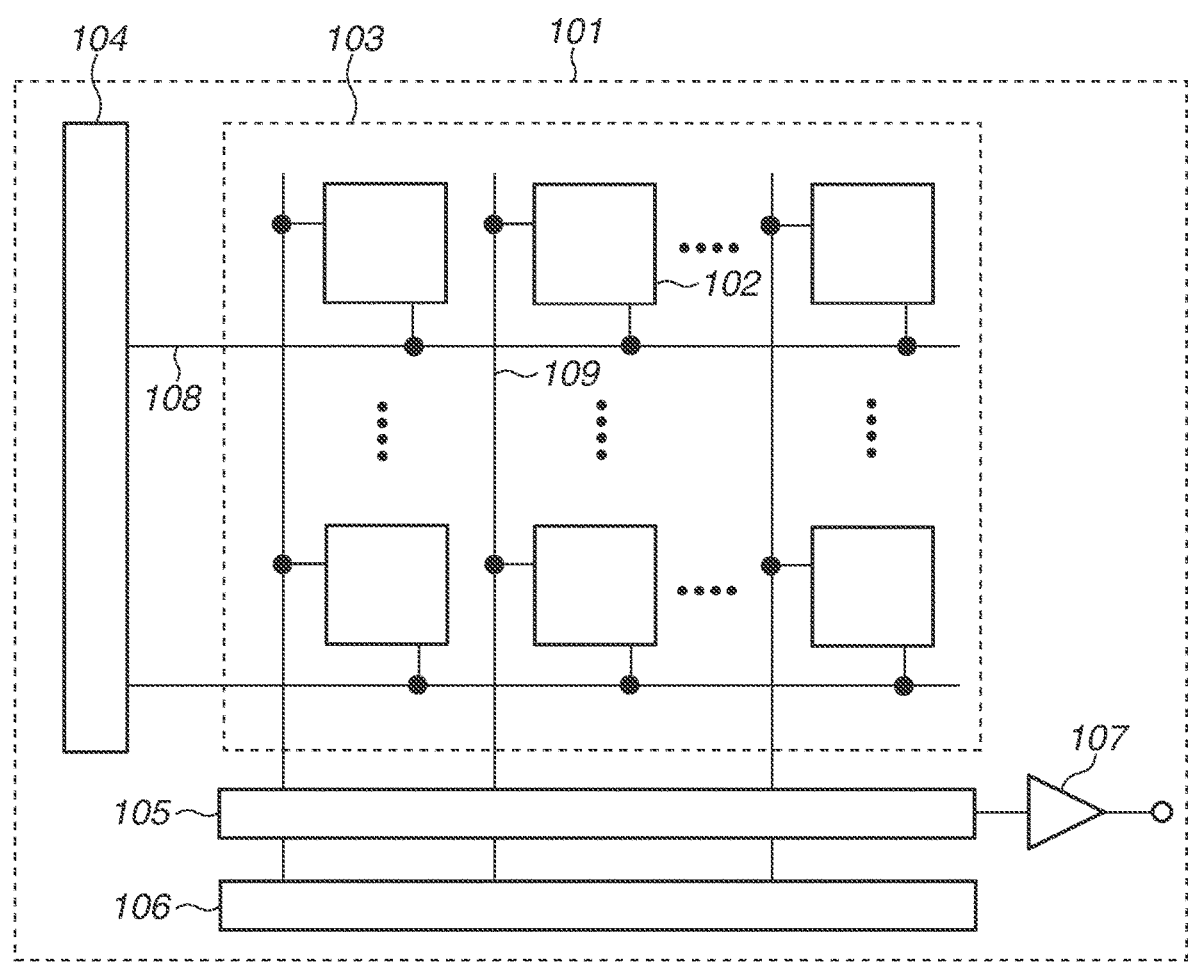
FIG. 1 is a system diagram illustrating an example of a portion of a photoelectric conversion apparatus according to a first exemplary embodiment.

Various exemplary embodiments of the present disclosure will be described below with reference to the drawings. It should be noted that the exemplary embodiments disclosed herein are mere examples of the present disclosure and that the numerical values, shapes, materials, components, and arrangements and connection forms of components are not intended to limit the scope of the present disclosure. Further, components having the same or similar function are given the same reference numeral in the drawings, and descriptions thereof are sometimes omitted or simplified.

The exemplary embodiments of the present disclosure are not limited to those disclosed herein, and various modifications can be made. For example, an example in which a portion of a configuration according to an exemplary embodiment is added to another exemplary embodiment and an example in which a portion of a configuration according to an exemplary embodiment replaces a portion of a configuration of another exemplary embodiment are also exemplary embodiments of the present disclosure. In other words, the present disclosure can be implemented in various forms within the technical concept or major features of the present disclosure.

In the following descriptions, a semiconductor region of a first conductivity type where a majority carrier is a carrier that is the same as a signal carrier is an n-type semiconductor region, and a second conductivity type semiconductor region is a p-type semiconductor region. In other words, the signal carrier is an electron. Further, an anode and cathode of a photoelectric conversion portion are respectively n-type and p-type. The polarity and conductivity types can all be reversed. More specifically, the signal carrier can be a hole, and the semiconductor region of the first conductivity type and the semiconductor region of the second conductivity type can respectively be a p-type semiconductor region and an n-type semiconductor region. Further, the anode and cathode of the photoelectric conversion portion can be p-type and n-type, respectively. In this case, a voltage relationship is reversed.

FIG. 1 is a system diagram schematically illustrating a photoelectric conversion apparatus according to a first exemplary embodiment. A photoelectric conversion apparatus 101 includes a unit array 103 and a driving circuit unit. The driving circuit unit includes a circuit that controls driving of the unit array 103. The unit array 103 includes a plurality of photoelectric conversion units 102 arranged, positioned, or disposed in first and second directions. The second direction intersects with the first direction. Each photoelectric conversion unit 102 includes a photoelectric conversion portion described below. For example, the first direction is a row direction, and the second direction is a column direction. In a case where the photoelectric conversion apparatus 101 is used as an image capturing apparatus, the plurality of photoelectric conversion units 102 can constitute pixels.

The driving circuit unit includes a vertical scan circuit 104, a column circuit 105, a horizontal scan circuit 106, and an output circuit 107. In the unit array 103, a first scan line 108 is arranged, positioned, or disposed along the first direction for each unit row. Further, a signal line 109 is arranged along the second direction for each unit column.

Each first scan line 108 is connected to an output end of the corresponding row of the vertical scan circuit 104. Further, each signal line 109 is connected to an input end of the column circuit 105. In FIG. 1, the driving circuit unit is arranged, positioned, or disposed near the unit array 103. The arrangement position of the driving circuit unit is not limited thereto. For example, in a case where the photoelectric conversion apparatus 101 is a stacked photoelectric conversion apparatus, the driving circuit unit can be arranged in a region that overlaps the plurality of photoelectric conversion units 102 in planar view. As used herein, the term "plane" refers to a plane that is parallel to a light incidence surface of a substrate including the photoelectric conversion portions when viewed from a normal line direction with respect to a surface parallel to the light incidence surface.

The photoelectric conversion unit 102 converts light into an electric signal and outputs the electric signal to the column circuit 105 via the signal line 109.

The vertical scan circuit 104 feeds a row selection signal to the first scan line 108 when the photoelectric conversion unit 102 outputs the electric signal.

The column circuit 105 performs predetermined processing (e.g., noise removal and signal amplification) on the electric signal input from the photoelectric conversion unit 102 and then outputs the processed signal to the output circuit 107.

The horizontal scan circuit 106 feeds to the column circuit 105 a control signal for sequentially outputting the signal processed by the column circuit 105 to the output circuit 107.

The output circuit 107 outputs the signal output from the column circuit 105 to an external recording unit of the photoelectric conversion apparatus 101 or a signal processing unit.

Figure 2:
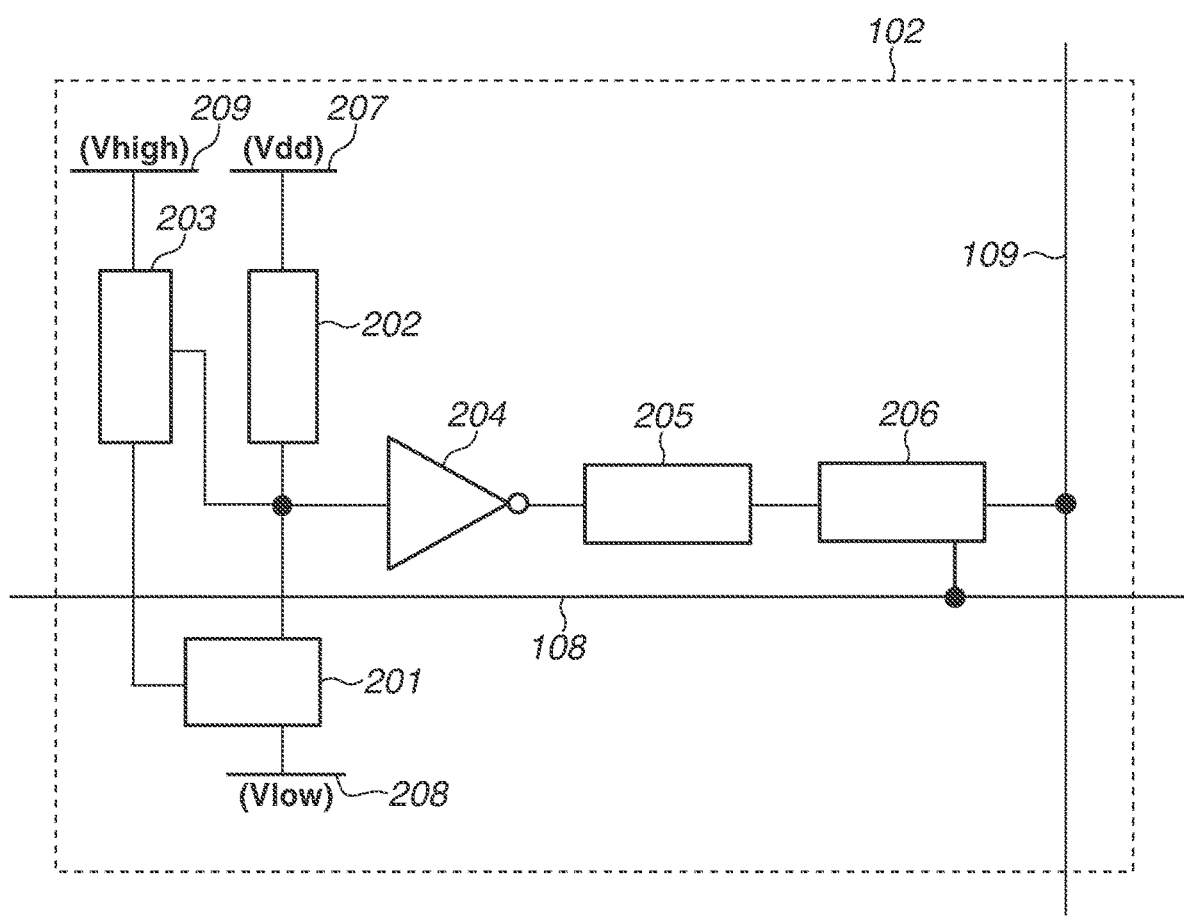
FIG. 2 is a block diagram illustrating an example of a circuit of a photoelectric conversion unit of the photoelectric conversion apparatus according to the first exemplary embodiment.

FIG. 2 is a circuit diagram illustrating the photoelectric conversion unit 102 of the photoelectric conversion apparatus 101. As illustrated in FIG. 2, the photoelectric conversion unit 102 includes the photoelectric conversion portion 201, a first control unit 202, a second control unit 203, a waveform shaping unit 204, a counter circuit 205, and a selection circuit 206.

A first voltage Vdd is fed to the photoelectric conversion portion 201 from a first wire 207 via the first control unit 202. A second voltage Vlow is fed to the photoelectric conversion portion 201 from a second wire 208. The photoelectric conversion portion 201 includes an embedded electrode illustrated in FIG. 3. A third voltage Vhigh is fed to the embedded electrode from a third wire 209 via the second control unit 203. The third voltage Vhigh, the first voltage Vdd, and the second voltage Vlow are set to decrease in this order. The first voltage Vdd is set so that the potential difference between the first voltage Vdd and the second voltage Vlow becomes smaller than the potential difference between the second voltage Vlow and the third voltage Vhigh. The third voltage Vhigh is set so that an avalanche multiplication region R is generated between the photoelectric conversion portion 201 and the embedded electrode.

The photoelectric conversion portion 201 can be configured by an avalanche diode (AD). The AD can be either one of an avalanche photodiode (APD), which performs avalanche multiplication in a linear mode, and a single photon avalanche diode (SPAD), which performs avalanche multiplication in a Geiger mode. Desirably, a SPAD is used. Hereinafter, a SPAD will be described as an example.

A signal carrier generated by the photoelectric conversion portion 201 based on light incident on the photoelectric conversion portion 201 is accelerated at the avalanche multiplication region R and undergoes avalanche multiplication. Consequently, the potential of an anode of the photoelectric conversion portion 201 decreases. A current generated by avalanche multiplication flows into the second wire 208 via a connection node of the first control unit 202, the waveform shaping unit 204, and the photoelectric conversion portion 201.

The first control unit 202 is connected to the first wire 207 and the photoelectric conversion portion 201. The first control unit 202 is, for example, a load circuit such as a quenching circuit composed of a positive (or p-channel) metal oxide semiconductor (PMOS) transistor. The first control unit 202 controls the potential of the connection node to return to the first voltage Vdd based on a current flowing in the connection node of the photoelectric conversion portion 201 and the first control unit 202. More specifically, avalanche multiplication occurs at the avalanche multiplication region R, and the potential of the anode decreases, and the potential of the connection node becomes lower than the first voltage Vdd. If a predetermined threshold value is exceeded, the first voltage Vdd is applied to the anode of the photoelectric conversion portion 201 via the first control unit 202.

The waveform shaping unit 204 shapes a waveform based on the potential of the anode of the photoelectric conversion portion 201. More specifically, the potential of the connection node is input to the waveform shaping unit 204. The waveform shaping unit 204 outputs a digital signal based on whether a threshold value of the waveform shaping unit 204 is exceeded, and inputs the digital signal to the counter circuit 205. The waveform shaping unit 204 composed, for example, of an inverter circuit.

The second control unit 203 is connected to the third wire 209 and the photoelectric conversion portion 201 and feeds a predetermined voltage to the embedded electrode of the photoelectric conversion portion 201. The potential of the connection node can be input to the second control unit 203. There may be a case where the first control unit 202 cannot control the potential of the connection node to the first voltage Vdd. In other words, the potential of the connection node may not return to a state where the potential exceeds the threshold value of the waveform shaping unit 204 and remains lower than the threshold value. Even in this case, the voltage to be applied to the embedded electrode by the second control unit 203 is controlled by inputting the potential of the connection node to the second control unit 203.

More specifically, in a case where an input potential exceeds the threshold value, the second control unit 203 controls the voltage to be applied to the photoelectric conversion portion 201 to a voltage at which the avalanche multiplication region R is not generated at the photoelectric conversion portion 201. For example, the same voltage as the first voltage Vdd is applied. As a result, avalanche multiplication does not occur, and the potential of the connection node changes toward the first voltage Vdd. Then, the potential of the connection node is changed to a state where the potential does not exceed the threshold value of the waveform shaping unit 204, and the waveform shaping unit 204 can shape waveforms. In the state where the potential of the connection node does not exceed the threshold value, the second control unit 203 electrically connects the third wire 209 and the photoelectric conversion portion 201. Then, the state where the avalanche multiplication region R is generated can be restored. As described above, the second control unit 203 can change the voltage to be applied to the embedded electrode of the photoelectric conversion portion 201. The second control unit 203 can be composed of a negative (or n-channel) metal oxide semiconductor (NMOS) transistor or switch.

The counter circuit 205 counts the number of photons generated by the photoelectric conversion portion 201 based on a signal output by the waveform shaping unit 204. The counter circuit 205 is connected to the signal line 109 via the selection circuit 206.

A row selection signal is fed to the selection circuit 206 via the first scan line 108, and an electrical connection and an electrical disconnection between the counter circuit 205 and the signal line 109 are switched.

Figure 3:
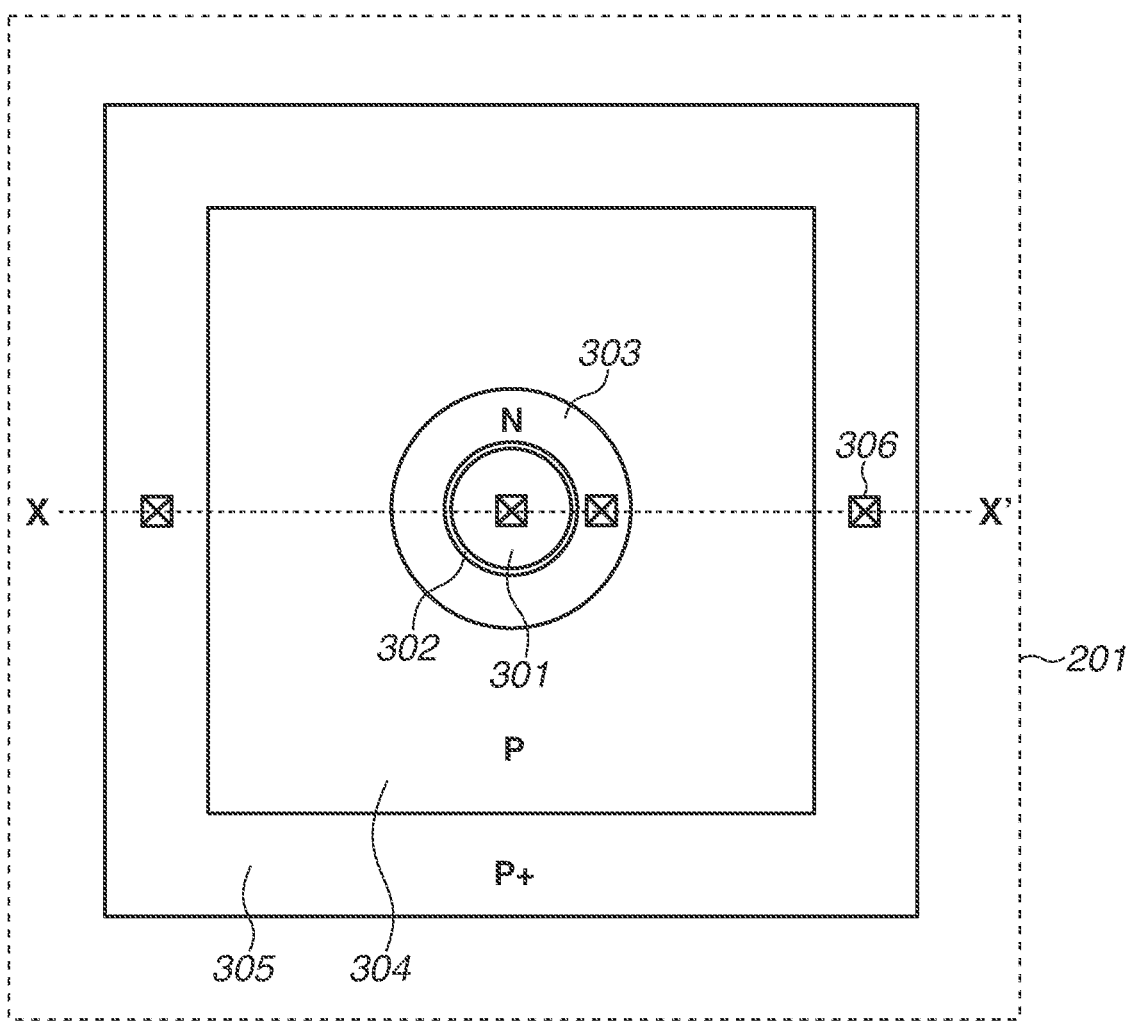
FIG. 3 is a plan view illustrating a photoelectric conversion portion of the photoelectric conversion apparatus according to the first exemplary embodiment.

FIG. 3 is a plan view illustrating the photoelectric conversion portion 201. An insulation member 302, an n-type semiconductor region 303 (first semiconductor region), and p-type semiconductor regions 304 and 305 are arranged, positioned, or disposed around the embedded electrode 301. The insulation member 302 is arranged, positioned, or disposed to surround the embedded electrode 301 in planar view. The embedded electrode 301 is connected to the second control unit 203. The n-type semiconductor region 303 is the anode of the photoelectric conversion portion 201 and is connected to the first control unit 202. The p-type semiconductor regions 304 and 305 each are a cathode and both of them are connected to the second wire 208.

In FIG. 3, the embedded electrode 301, the insulation member 302, and the n-type semiconductor region 303 each have a circular outer periphery in planar view of a surface (first surface) of the semiconductor substrate that includes a contact plug 306. Alternatively, the outer peripheries can be polygonal. Further, while the p-type semiconductor regions 304 and 305 each have a polygonal outer periphery, the outer peripheries can be circular.

Figure 4:
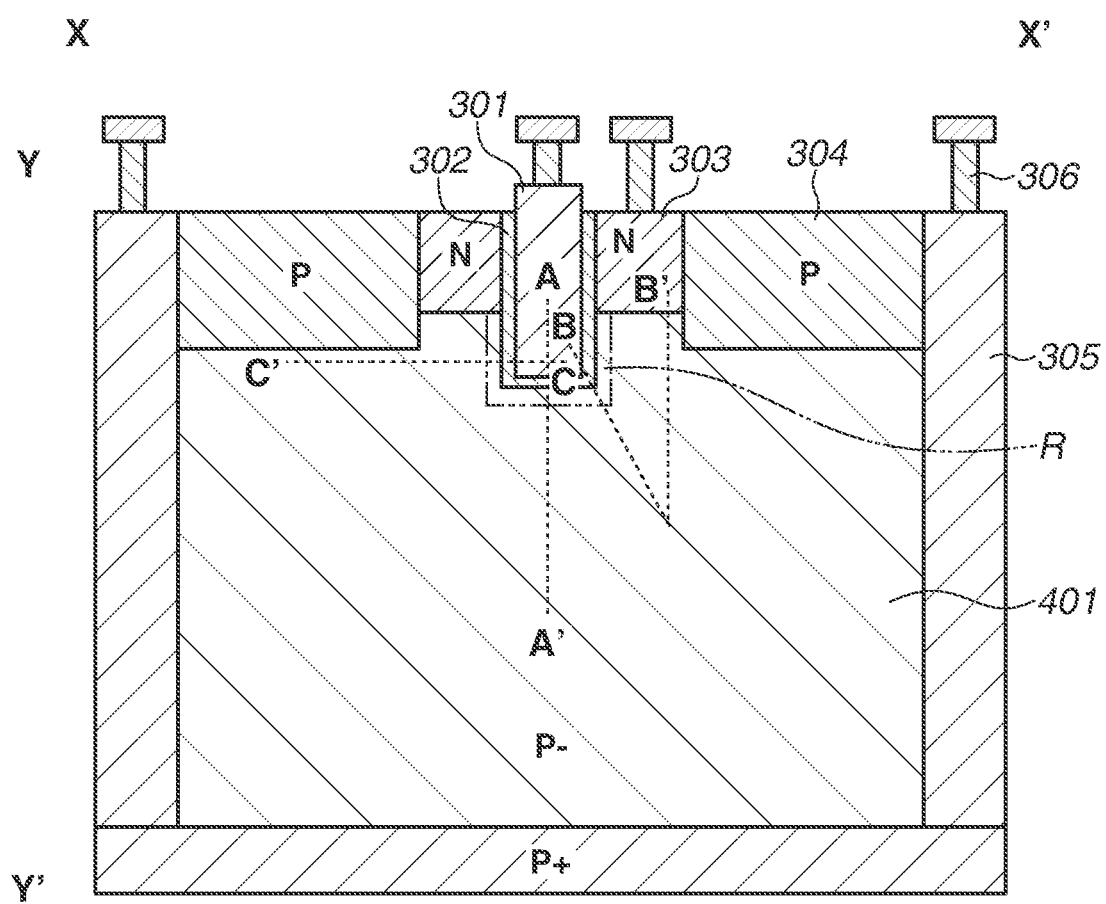
FIG. 4 is a cross-sectional view illustrating the photoelectric conversion portion of the photoelectric conversion apparatus according to the first exemplary embodiment.

FIG. 4 is a cross-sectional view taken along X-X' specified in FIG. 3. Hereinafter, the first surface of the semiconductor substrate will be referred to as "upper surface" and a second surface opposite to the first surface as "lower surface". Further, the term "depth direction" refers to a direction from the first surface toward the second surface. A lower surface of the n-type semiconductor region 303 is in the semiconductor substrate. Under the n-type semiconductor region 303 is a p-type semiconductor region 401 (second semiconductor region). The p-type semiconductor region 401 is typically a well region. The p-type semiconductor region 401 overlaps the n-type semiconductor region 303 in planar view. The p-type semiconductor region 401 has a lower impurity concentration than those of the p-type semiconductor regions 304 and 305.

The deepest portion (leading edge portion) of the embedded electrode 301 is desirably at a position deeper than the lower surface of the n-type semiconductor region 303 but can be at a position shallower than the n-type semiconductor region 303. The embedded electrode 301 is arranged, positioned, or disposed so that at least the avalanche multiplication region R generated between the embedded electrode 301 and the p-type semiconductor region 401 is in contact with the n-type semiconductor region 303. It is easier to collect an avalanche-multiplied signal carrier at the n-type semiconductor region 303 in a case where the leading edge portion is at a deeper position than the lower surface of the n-type semiconductor region 303 than in a case where the leading edge portion is at a shallower position than the lower surface of the n-type semiconductor region 303. For the same reason, the deepest portion of the embedded electrode 301 is desirably at a position deeper than a p-n junction surface of the p-type semiconductor region 401 and the n-type semiconductor region 303. In other words, the distance between the second surface of the semiconductor substrate and the p-n junction surface is desirably longer than the distance between the second surface of the semiconductor substrate and the deepest portion of the embedded electrode 301.

The p-type semiconductor region 304 (third portion) is formed between the first surface and the p-type semiconductor region 401. The p-type semiconductor region 304 reduces dark electrons generated at the first surface. The p-type semiconductor region 304 may be a low-concentration n-type semiconductor region. In this case, dark electrons generated at a surface flow into the first wire 207 via the n-type semiconductor regions 303 and 304.

The p-type semiconductor region 305 isolates the photoelectric conversion portions 201 of the adjacent photoelectric conversion units 102. The p-type semiconductor region 304 has a lower impurity concentration than that of the p-type semiconductor region 305. This prevents unintended avalanche multiplication between the n-type semiconductor region 303 and the p-type semiconductor region 304.

The embedded electrode 301 may be configured of, for example, a semiconductor such as polysilicon, a metal, or a compound semiconductor. Further, the insulation member 302 is composed of, for example, a silicon oxide film. The thickness of the insulation member 302 is set as appropriate so that the embedded electrode 301 and the p-type semiconductor region 401 cause avalanche multiplication and signal carriers do not pass through the insulation member 302. The thickness of the insulation member 302 is desirably thinner than the embedded electrode 301 in a direction parallel to the first surface.

Before an avalanche current is generated, the n-type semiconductor region 303 and the embedded electrode 301 are set to voltages substantially equal to Vdd 207 and Vhigh 209, respectively. The potential difference (hereinafter, "Vpn") between the p-type semiconductor region 401 and the n-type semiconductor region 303 is "Vpn=Vdd−Vlow" and is less than a threshold value for an occurrence of avalanche multiplication. In other words, the first voltage Vdd and the second voltage Vlow are set so that a strong electric field region (avalanche multiplication region R) where avalanche multiplication occurs is not generated at the p-n junction surface. Further, the potential difference (hereinafter, "Vmp") between the embedded electrode 301 and the p-type semiconductor region 401 is "Vmp=Vhigh−Vlow" and is greater than or equal to the threshold value for an occurrence of avalanche multiplication.

The avalanche multiplication region R and the n-type semiconductor region 303 are in contact with each other. With this configuration, signal carriers amplified at the avalanche multiplication region R can flow into the n-type semiconductor region 303. The n-type semiconductor region 303 constitutes a portion of the first surface of the semiconductor substrate. Thus, the n-type semiconductor region 303 and the contact plug for reading signal carriers from the n-type semiconductor region 303 can be connected with ease. It is not essential, however, to constitute a portion of the first surface of the semiconductor substrate. If, for example, a portion of the semiconductor substrate is removed so as to contact the n-type semiconductor region 303 and the contact plug, signal carriers can be read.

Light incident on the photoelectric conversion portion 201 is photoelectrically converted mainly at the p-type semiconductor region 401 to generate signal carriers. The generated signal carriers move toward the embedded electrode 301 along a potential gradient illustrated in FIGS. 5A and 5B. Then, the signal carriers are accelerated by the avalanche multiplication region R generated near the embedded electrode 301, and avalanche multiplication occurs to generate an avalanche current. At this time, the generated avalanche current (hereinafter, "IaV") flows between the n-type semiconductor region 303 and the p-type semiconductor region 401. Thus, when the avalanche current flows, the power consumption (hereinafter, "Pav") is "Pav=Iav·xVpn".

Figure 5A:
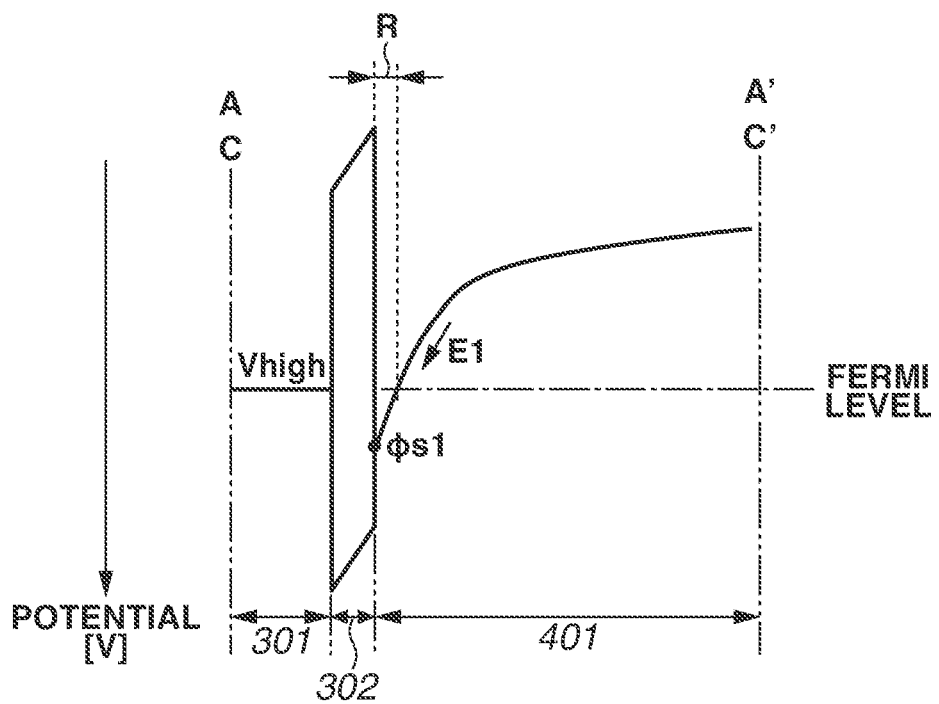
FIGS. 5A and 5B are graphs each illustrating a potential of the photoelectric conversion portion of the photoelectric conversion apparatus according to the first exemplary embodiment.
Figure 5B:
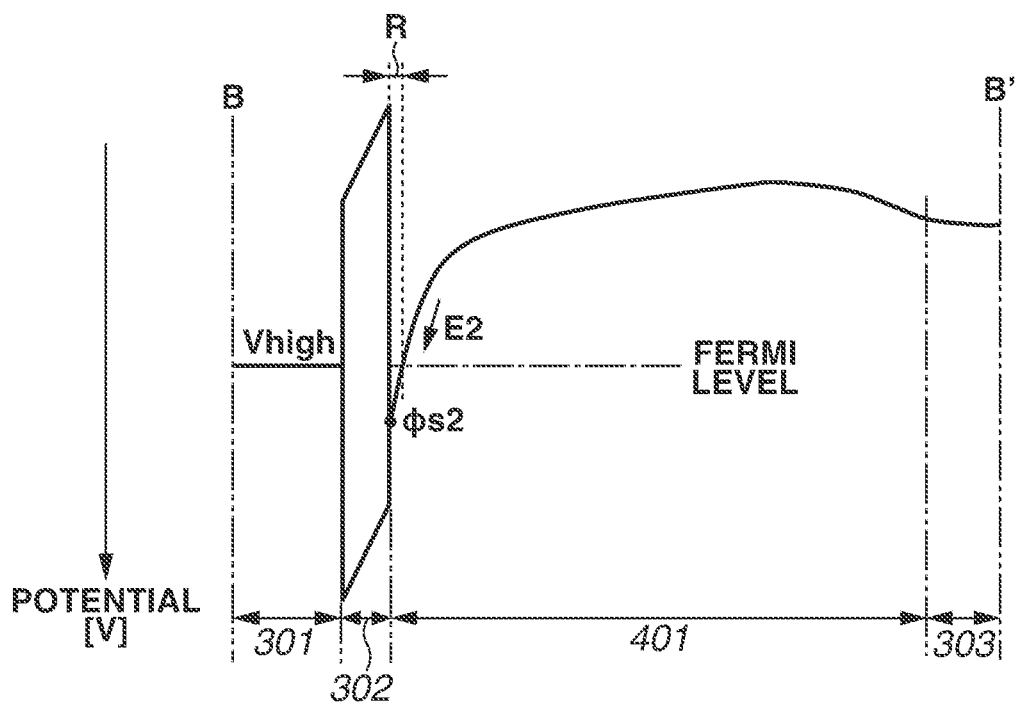

In FIG. 5B, the potential of the n-type semiconductor region 303 is higher than a potential of a neighborhood of the insulation member 302. As described above, if avalanche multiplication occurs, the potential to be applied to the embedded electrode 301 by the second control unit 203 is changed to a potential at which the avalanche multiplication region R is not generated. As a result of the potential change, the potential of the neighborhood of the insulation member 302 increases and becomes close to the level of the potential of the n-type semiconductor region 303. By changing the level of the potential of the neighborhood of the insulation member 302 as described above, charge remaining at the avalanche multiplication region R is reduced, and the avalanche current is efficiently passed to the n-type semiconductor region 303. It is not essential, however, to change the level of the potential of the neighborhood of the insulation member 302. Even in a case where the level of the potential of the neighborhood of the insulation member 302 is not changed, if avalanche multiplication occurs, the avalanche current flows into the n-type semiconductor region 303. Thus, an advantage that the power consumption is reduced is obtained without changing the potential of the neighborhood of the insulation member 302.

A case where a voltage is applied to an n-type semiconductor region and a p-type semiconductor region so that avalanche multiplication occurs at an interface between the n-type semiconductor region and the p-type semiconductor region will be described below with reference to a photoelectric conversion apparatus discussed in Japanese Patent Application Laid-Open No. 2018-19040 as an example. In the photoelectric conversion apparatus discussed in Japanese Patent Application Laid-Open No. 2018-19040, a potential difference sufficiently greater than Vpn is applied across a p-n junction. More specifically, a potential difference that causes avalanche multiplication is applied across the p-n junction. In this case, avalanche multiplication occurs across the p-n junction, and the power consumption is higher than that in the present exemplary embodiment.

On the contrary, according to the present exemplary embodiment, avalanche multiplication occurs not across the p-n junction but at another region, and a strong electric field is not generated and avalanche multiplication is not generated across the p-n junction. This achieves reduced power consumption compared to the photoelectric conversion apparatus discussed in Japanese Patent Application Laid-Open No. 2018-19040.

Light incident on the photoelectric conversion portion 201 may enter from the first surface side or from the second surface side of the semiconductor substrate. More specifically, the direction may be either from Y to Y' or from Y' to Y in FIG. 4. Desirably, light enters from the second surface. This prevents incident light from being blocked by the contact plug and the lines.

FIG. 5A illustrates potential shapes between A and A' and between C and C' in FIG. 4, and FIG. 5B illustrates a potential shape between B and B' in FIG. 4. In FIGS. 5A and 5B, a potential gradient in the p-type semiconductor region 401 becomes the maximum at the neighborhood of the insulation member 302, and maximum electric field intensities are respectively E1 and E2. Electric field concentration is more likely to occur at corner portions of the embedded electrode 301 than flat portions such as side surfaces of the embedded electrode 301. Thus, the electric field intensity increases at the corner portions of the embedded electrode 301, so that E2>E1. Signal carriers are accelerated by E1 and E2, and avalanche multiplication occurs.

Further, the surface potentials (potentials at a surface in contact with the insulation member 302) of the p-type semiconductor region 401 are respectively $\Phi s1$ and $\Phi s2$. The surface potentials are changed to potentials higher than or equal to the Fermi level (Vhigh in the present exemplary embodiment) so that an inversion layer is formed at an interface between the p-type semiconductor region 401 and the insulation member 302. In the case where the inversion layer is formed, avalanche multiplication occurs between the inversion layer and the p-type semiconductor region 401. However, the inversion layer does not necessarily have to be formed.

The first control unit 202 and the second control unit 203 do not both have to be provided, and only one of the first control unit 202 and the second control unit 203 may be provided. Further, in a case where the voltage to be fed from the third wire 209 is fixed to the third voltage Vhigh, the second control unit 203 is connected to the first wire 207, and the electrical connection of the second control unit 203 may be switched between the first wire 207 and the third wire 209. Further, a fourth wire that feeds a voltage different from that fed by the first wire 207 may be provided, and the electrical connection may be switched between the fourth wire and the first wire 207.

According to the present exemplary embodiment, the power consumption can be reduced compared to the photoelectric conversion apparatus discussed in Japanese Patent Application Laid-Open No. 2018-19040.

A second exemplary embodiment will be described with reference to FIGS. 6, 7A, and 7B. The present exemplary embodiment is different from the first exemplary embodiment in that a p-type semiconductor region 601 (second portion) having an impurity concentration higher than the impurity concentration of the p-type semiconductor region 401 is arranged, positioned, or disposed in the neighborhood of the deepest portion (leading edge) of the embedded electrode 301. Descriptions of the portions similar to those in the first exemplary embodiment are omitted, and mainly differences from the first exemplary embodiment will be described below.

Figure 6:
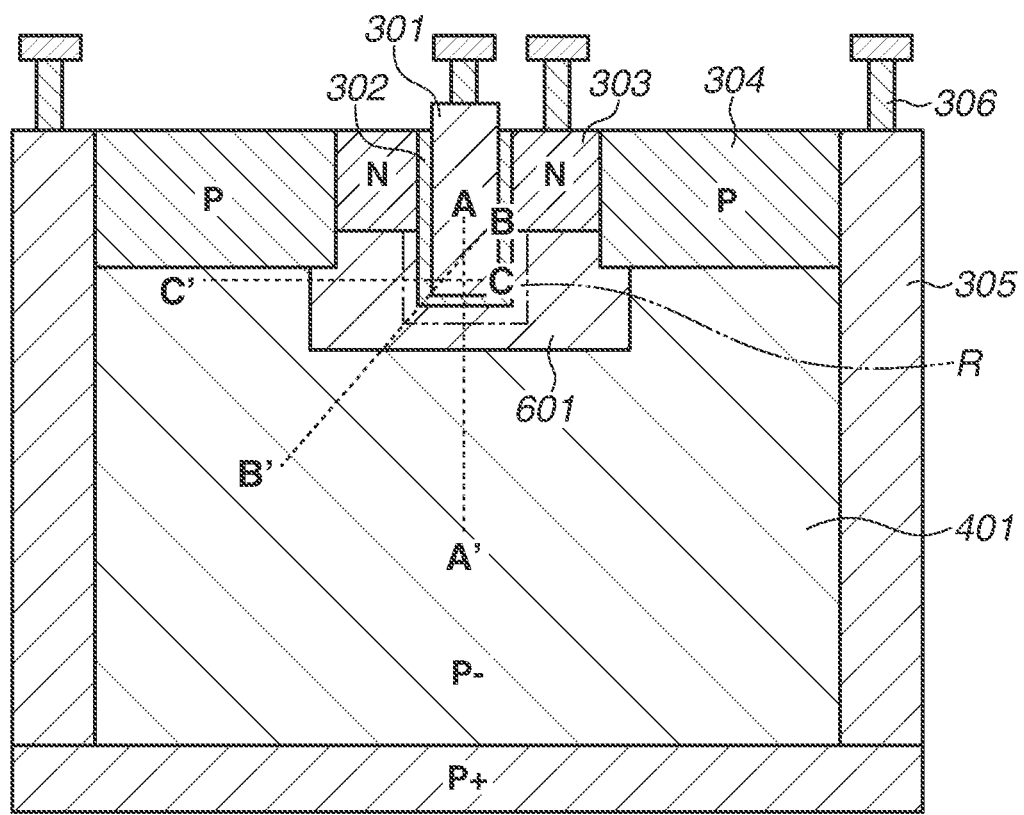
FIG. 6 is a cross-sectional view illustrating a photoelectric conversion unit of another photoelectric conversion apparatus according to a second exemplary embodiment.

FIG. 6 is a cross-sectional view illustrating the photoelectric conversion portion 201 according to the present exemplary embodiment. The p-type semiconductor region 601 is arranged, positioned, or disposed in the neighborhood of the leading edge of the embedded electrode 301. The p-type semiconductor region 601 is arranged, positioned, or disposed under the n-type semiconductor region 303. The p-type semiconductor region 601 overlaps the n-type semiconductor region 303 in planar view. The impurity concentration of the p-type semiconductor region 601 is higher than the impurity concentration of the p-type semiconductor region 601. Thus, the intensity of an electric field generated between the embedded electrode 301 and the p-type semiconductor region 601 is higher than that in the first exemplary embodiment. The p-type semiconductor region 601 is continuously arranged, positioned, or disposed along the embedded electrode 301.

Figure 7A:
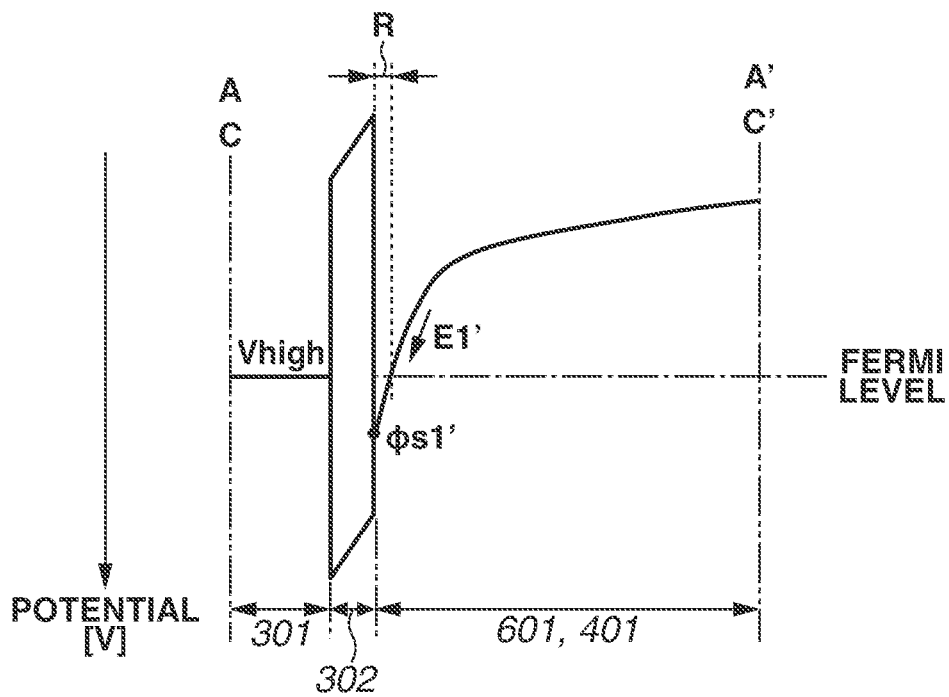
FIGS. 7A and 7B are graphs each illustrating a potential of a photoelectric conversion portion of the other photoelectric conversion apparatus according to the second exemplary embodiment.
Figure 7B:
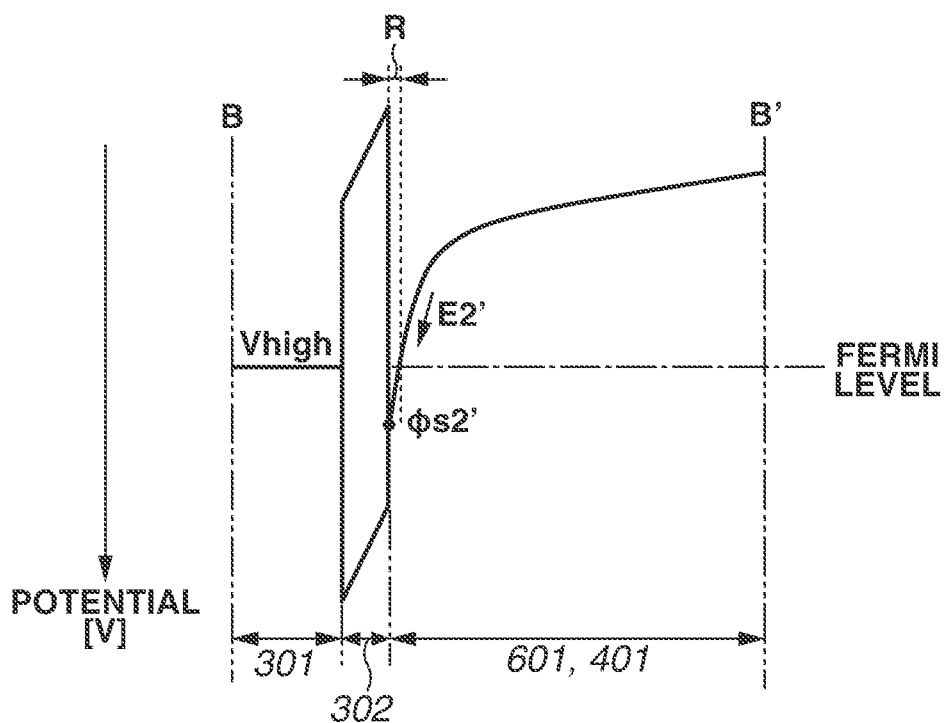

FIG. 7A illustrates potential shapes between A and A' and between C and C' in FIG. 6, and FIG. 7B illustrates a potential shape between B and B' in FIG. 6. In FIGS. 7A and 7B, potential gradients in the p-type semiconductor region 601 and the p-type semiconductor region 401 become the maximum at the neighborhood of the insulation member 302, and maximum electric field intensities are respectively E1' and E2'. The corner portions of the embedded electrode 301 are more affected by electric field concentration than the flat portions of the side surfaces. Thus, the electric field intensity increases at E2', so that E2'>E1'. Further, when E1' and E2' are compared with E1 and E2 in the first exemplary embodiment, E1'>E1 and E2'>E2. Thus, electrons are accelerated by E1' and E2', and avalanche multiplication occurs.

Further, the surface potentials of the p-type semiconductor region 601 are respectively $\Phi s1'$ and $\Phi s2'$, and the surface potentials are changed to potentials higher than or equal to the Fermi level (Vhigh in the present exemplary embodiment) so that an inversion layer is formed at an interface between the p-type semiconductor region 601 and the insulation member 302. However, the inversion layer does not necessarily have to be formed.

While the p-type semiconductor region 401 is formed under the p-type semiconductor region 601 in FIG. 6, an n-type semiconductor region having a lower impurity concentration than the n-type semiconductor region 303 may be formed instead of the p-type semiconductor region 401.

In the present exemplary embodiment, avalanche multiplication is generated more easily, variations in output signals of the photoelectric conversion unit 102 are reduced, and stable photon detection is realized, compared to the first exemplary embodiment.

A third exemplary embodiment will be described with reference to FIGS. 8 and 9. The present exemplary embodiment is different from the first exemplary embodiment in that a ring-shaped embedded electrode is provided and that the ring-shaped embedded electrode is sandwiched between first conductivity type semiconductor regions. Descriptions of the portions similar to those in the first exemplary embodiment are omitted, and mainly differences from the first exemplary embodiment will be described.

Figure 8:
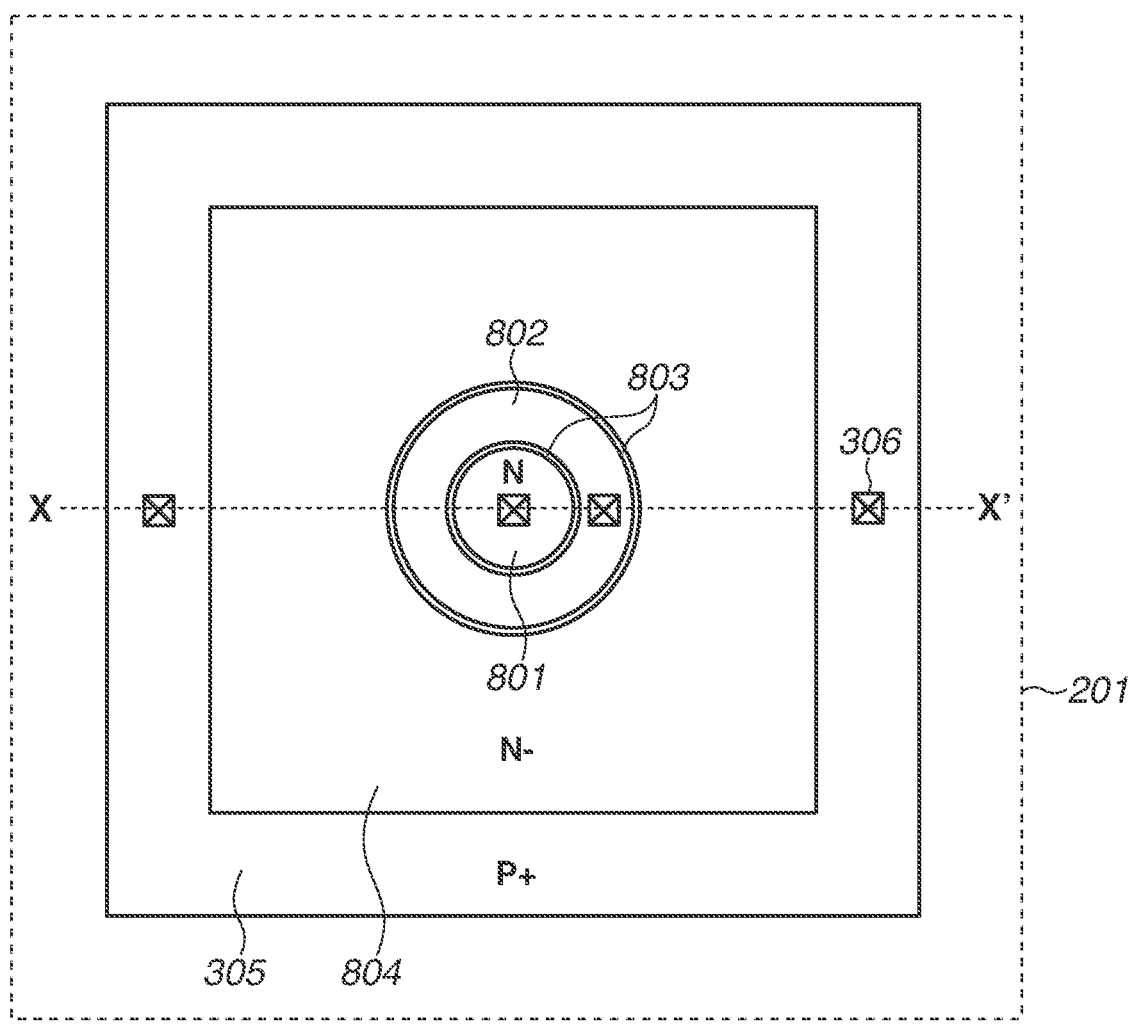
FIG. 8 is a plan view illustrating a photoelectric conversion portion of another photoelectric conversion apparatus according to a third exemplary embodiment.

FIG. 8 is a plan view of the photoelectric conversion portion 201. An insulation member 803 is arranged, positioned, or disposed to surround an n-type semiconductor region 801. Further, a ring-shaped embedded electrode 802 is arranged, positioned, or disposed to surround the insulation member 803. Further, the insulation member 803 is arranged, positioned, or disposed to surround the embedded electrode 802. Further, an n-type semiconductor region 804 is arranged to surround the insulation member 803. Further, the p-type semiconductor region 304 is arranged to surround the n-type semiconductor region 804.

The n-type semiconductor region 801 is connected to the first control unit 202. The embedded electrode 802 is connected to the second control unit 203. The p-type semiconductor region 304 is connected to the third wire 209.

In planar view, outer peripheries of the n-type semiconductor region 801 and the embedded electrode 802 are circular but may be polygonal. Further, an outer periphery of the n-type semiconductor region 804 is polygonal but may be circular.

Figure 9:
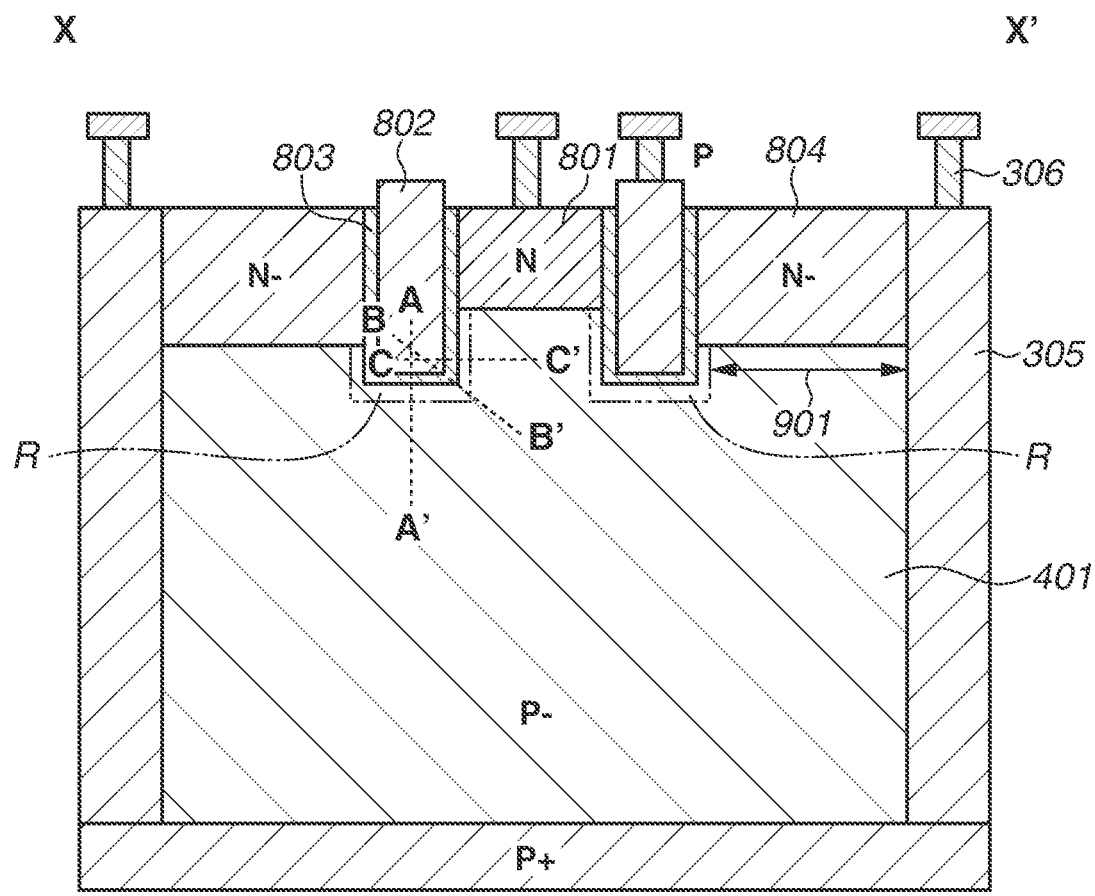
FIG. 9 is a cross-sectional view illustrating the photoelectric conversion portion of the other photoelectric conversion apparatus according to the third exemplary embodiment.

FIG. 9 is a cross-sectional view taken along X-X' illustrated in FIG. 8. Since the n-type semiconductor region 804 has a lower impurity concentration than that of the n-type semiconductor region 801, an electric field between the embedded electrode 802 and the n-type semiconductor region 804 is less likely to be strong. Thus, dark electrons generated in the neighborhood of the first surface of the semiconductor substrate are less likely to be avalanche-multiplied.

A distance 901 between the embedded electrode 802 and the p-type semiconductor region 305 is shorter than that in the first exemplary embodiment. Thus, signal carriers generated by photoelectric conversion in the neighborhood of the p-type semiconductor region 305 arrive at the avalanche multiplication region R formed in the neighborhood of the embedded electrode 802 within a shorter length of time, and avalanche multiplication is generated. The potential shapes between A and A', B and B', and C and C' are substantially the same as those in FIGS. 5A and 5B in the first exemplary embodiment.

With the arrangement according to the present exemplary embodiment, photons are detected at higher speed, so that the photoelectric conversion apparatus 101 is operated at higher speed.

A fourth exemplary embodiment will be described with reference to FIG. 10. The present exemplary embodiment is different from the third exemplary embodiment in that a p-type semiconductor region is provided in the neighborhood of the leading edge of the embedded electrode 802. Descriptions of the portions similar to those in the third exemplary embodiment are omitted, and mainly differences from the third exemplary embodiment will be described.

Figure 10:
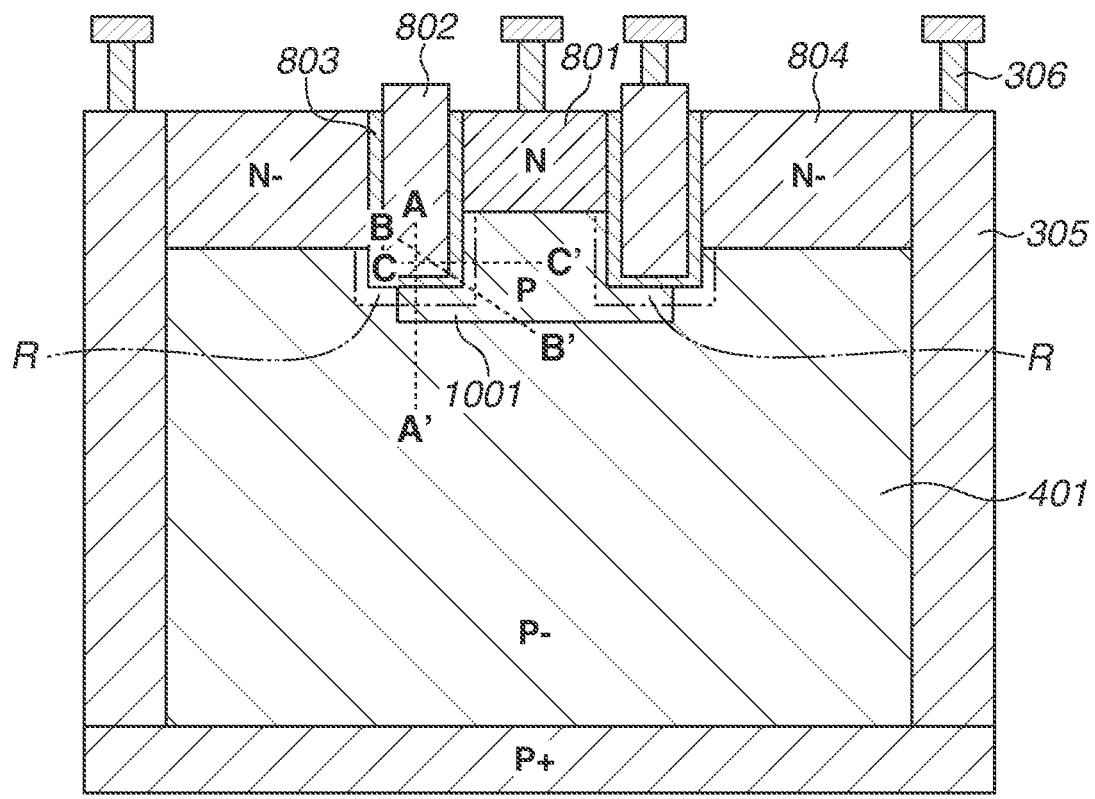
FIG. 10 is a cross-sectional view illustrating a photoelectric conversion portion of another photoelectric conversion apparatus according to a fourth exemplary embodiment.

FIG. 10 is a cross-sectional view illustrating the photoelectric conversion portion 201 according to the present exemplary embodiment. A p-type semiconductor region 1001 is arranged, positioned, or disposed in the neighborhood of the leading edge of the embedded electrode 802. The p-type semiconductor region 1001 has the same or similar functions as or to those of the p-type semiconductor region 601 according to the second exemplary embodiment. The p-type semiconductor region 1001 overlaps the n-type semiconductor region 801 in planar view. The p-type semiconductor region 1001 is arranged, positioned, or disposed under the n-type semiconductor region 801. The p-type semiconductor region 1001 has a higher impurity concentration than that of the p-type semiconductor region 401. Thus, the intensity of an electric field generated between the embedded electrode 802 and the p-type semiconductor region 1001 is higher than that in the third exemplary embodiment. The potential shapes between A and A', B and B', and C and C' are substantially the same as those in FIGS. 7A and 7B in the second exemplary embodiment.

While the p-type semiconductor region 401 is formed under the p-type semiconductor region 1001 in FIG. 10, an n-type semiconductor region having a lower impurity concentration than the n-type semiconductor region 303 may be formed instead of the p-type semiconductor region 401.

With the arrangement according to the present exemplary embodiment, avalanche multiplication is generated more easily, variations in output signals of the pixels of the photoelectric conversion unit 102 are reduced, and stable photon detection is achieved, compared to the third exemplary embodiment.

A fifth exemplary embodiment will be described with reference to FIGS. 11 and 12. The present exemplary embodiment is different from the fourth exemplary embodiment in that the first surface of the semiconductor substrate includes a p-type semiconductor region 1102. Descriptions of the portions similar to those in the fourth exemplary embodiment are omitted, and mainly differences from the fourth exemplary embodiment will be described.

Figure 11:
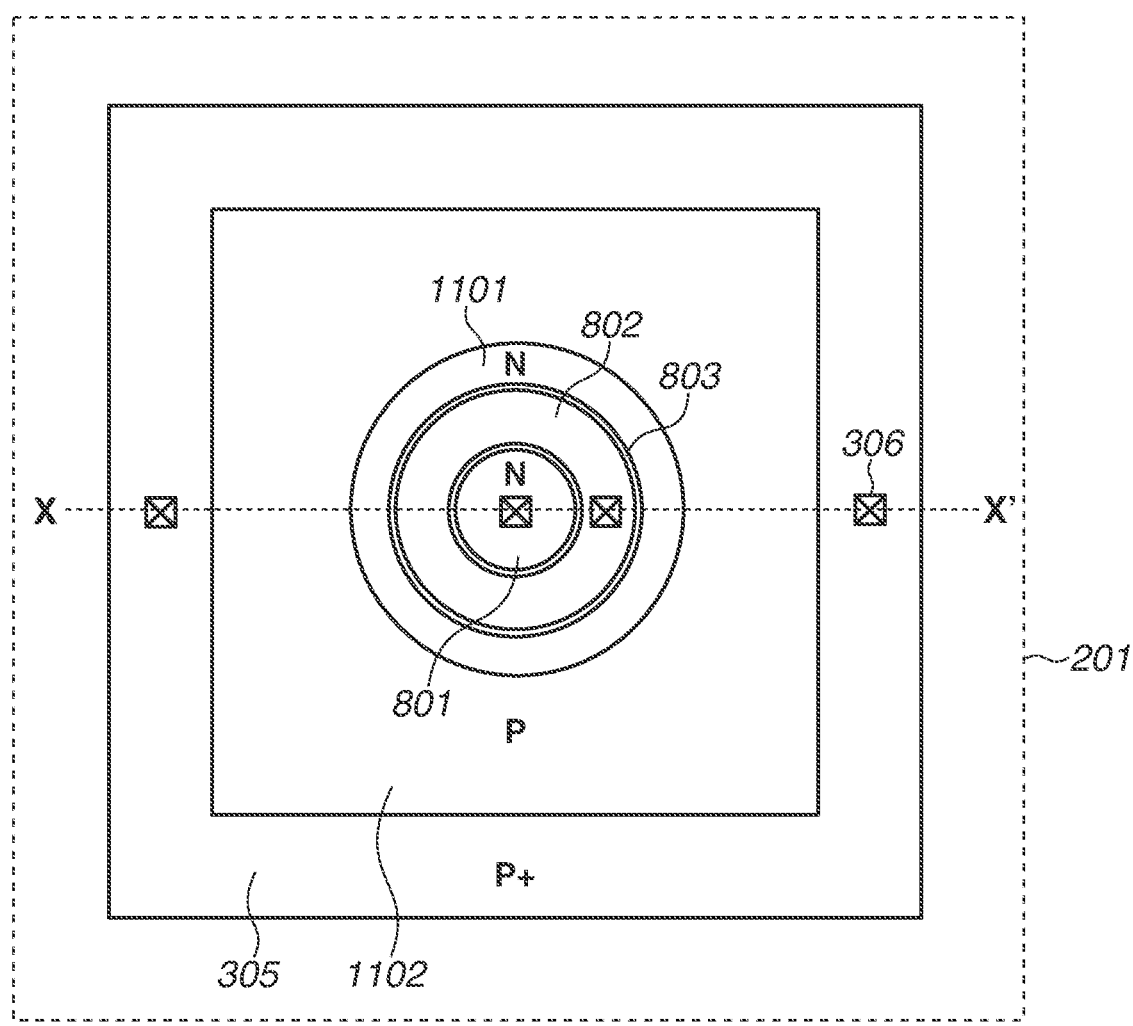
FIG. 11 is a plan view illustrating a photoelectric conversion portion of another photoelectric conversion apparatus according to a fifth exemplary embodiment.

FIG. 11 is a plan view of the photoelectric conversion portion 201. An n-type semiconductor region 1101 is arranged, positioned, or disposed to surround the ring-shaped embedded electrode 802. Further, the p-type semiconductor region 1102 is arranged, positioned, or disposed to surround the n-type semiconductor region 1101. Further, the p-type semiconductor region 305 is arranged to surround the p-type semiconductor region 1102. In other words, the p-type semiconductor region 1102 is arranged between the n-type semiconductor region 1101 and the p-type semiconductor region 305.

In planar view, an outer periphery of the n-type semiconductor region 1101 is circular but may be polygonal. Further, an outer periphery of the p-type semiconductor region 1102 is polygonal but may be circular.

Figure 12:
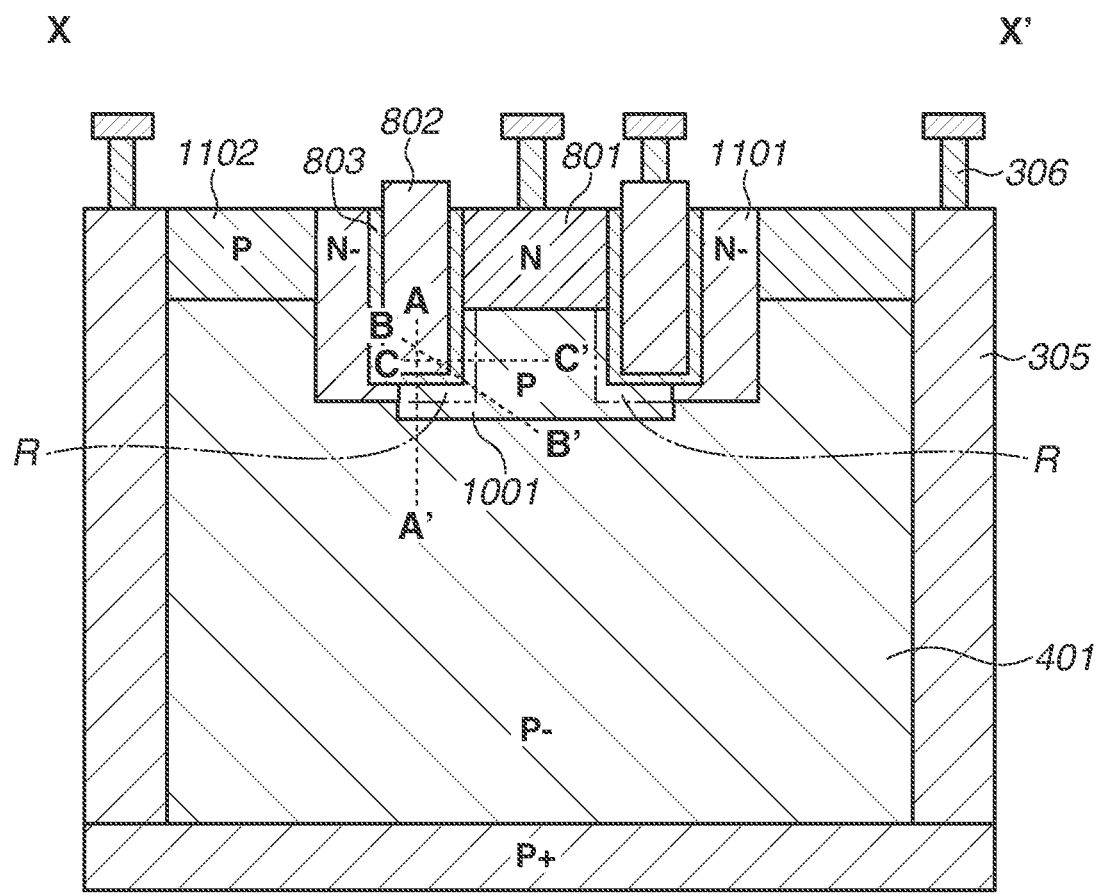
FIG. 12 is a cross-sectional view illustrating the photoelectric conversion portion of the other photoelectric conversion apparatus according to the fifth exemplary embodiment.

FIG. 12 is a cross-sectional view taken along X-X' illustrated in FIG. 11. The p-type semiconductor region 304 (third portion) is formed between the first surface and the p-type semiconductor region 401. The impurity concentration of the p-type semiconductor region 1102 is lower than the impurity concentration of the p-type semiconductor region 305 and higher than the impurity concentration of the p-type semiconductor region 401. The p-type semiconductor region 1102 has the same or similar functions as or to those of the p-type semiconductor region 304 according to the first exemplary embodiment. More specifically, the p-type semiconductor region 1102 suppresses dark electrons generated at the first surface. The p-type semiconductor region 304 is provided between the p-type semiconductor region 305 and the n-type semiconductor region 1101 so that generation of an unintended strong electric field region between the n-type semiconductor region 1101 and the p-type semiconductor regions 305 and 1102 is prevented. The potential shapes between A and A', B and B', and C and C' are substantially the same as those in FIGS. 7A and 7B in the second exemplary embodiment.

With the arrangement according to the present exemplary embodiment, dark electrons generated at the first surface of the semiconductor substrate are suppressed, in addition to the advantage of the fourth exemplary embodiment.

A sixth exemplary embodiment will be described with reference to FIG. 13. The present exemplary embodiment is different from the first exemplary embodiment in that a first substrate 1111 includes the photoelectric conversion portion 201, that a second substrate 1112 includes the waveform shaping unit 204, and that the first substrate 1111 and the second substrate 1112 are layered. Descriptions of the portions similar to the first exemplary embodiment are omitted, and mainly differences from the first exemplary embodiment will be described.

Figure 13:
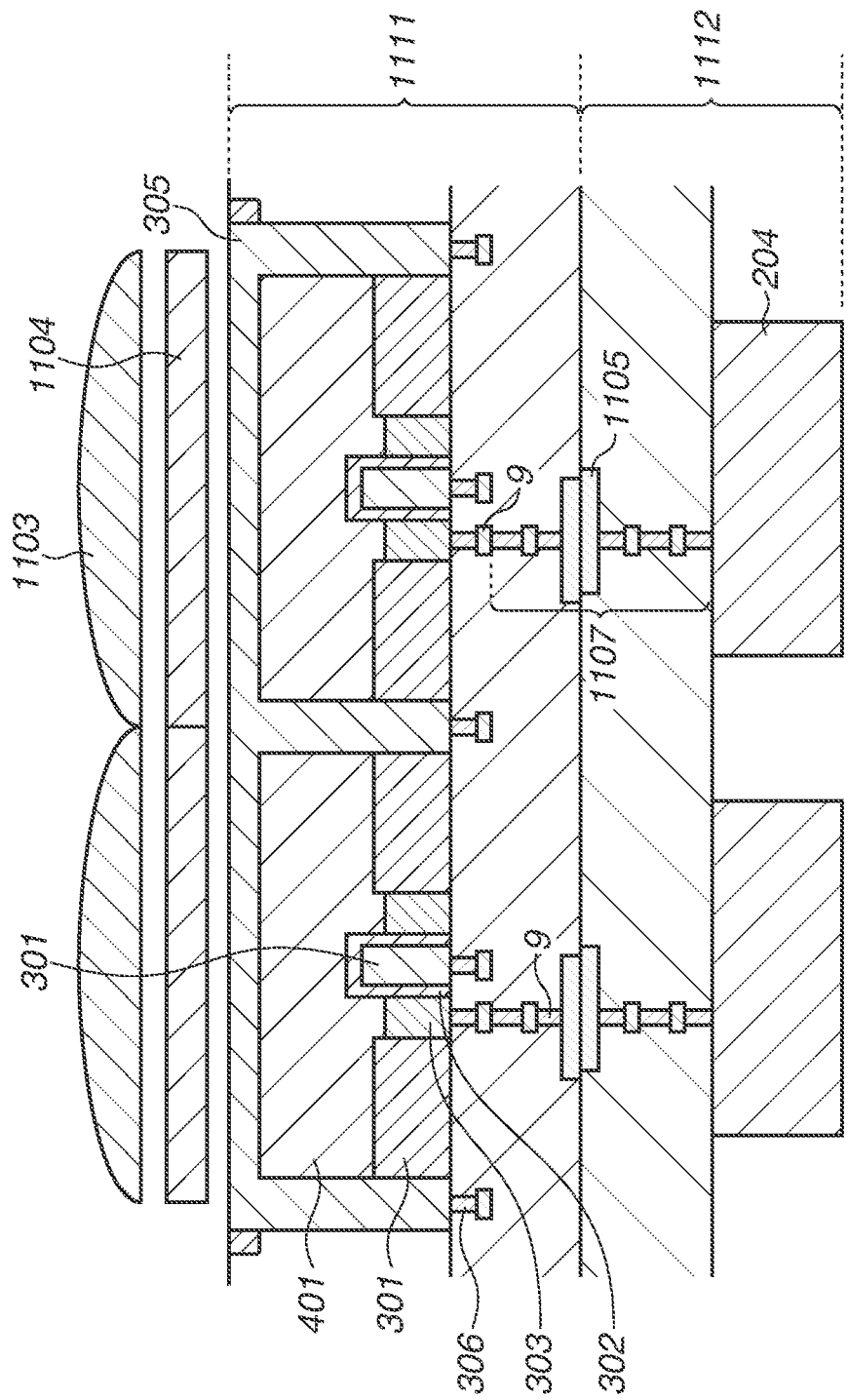
FIG. 13 is a cross-sectional view illustrating a photoelectric conversion apparatus according to a sixth exemplary embodiment.

In FIG. 13, the different semiconductor substrates respectively include the photoelectric conversion portion and the waveform shaping unit 204. The first substrate 1111 includes the plurality of photoelectric conversion portions. In FIG. 13, two photoelectric conversion portions 201 are arranged, positioned, or disposed as an example. The second substrate 1112 includes the waveform shaping unit 204, an interlayer insulation film, and a wire 1105. While the second substrate 1112 including the waveform shaping unit 204 and the wire 1105 is illustrated, the second substrate 1112 may include any other circuits. For example, the second substrate 1112 may include the counter circuit 205, the selection circuit 206, and the driving circuit unit.

The photoelectric conversion portion 201 has a back-illumination structure. More specifically, the wire 1105 and the second substrate 1112 are arranged, positioned, or disposed on the first surface side, and incident light travels in a direction from the second surface toward the first surface. At this time, the light travels through a microlens 1103 and a color filter 1104 and enters the p-type semiconductor region 401.

As described above, charge generated by photoelectric conversion at the p-type semiconductor region 401 travels through the p-type semiconductor region 401 and moves to the avalanche multiplication region R formed by the p-type semiconductor region 401 and the embedded electrode 301. Avalanche multiplication occurs at the avalanche multiplication region R, and a current flows into a wire 9 via the n-type semiconductor region 303.

According to the present exemplary embodiment, the first substrate 1111 including the photoelectric conversion portions 201 and the second substrate 1112 different from the first substrate 1111 are layered. The layered second substrate 1112 includes a processing circuit such as the counter circuit 205, so that an aperture ratio of the photoelectric conversion portion 201 increases, and light detection efficiency increases.

An example of a photoelectric conversion system according to a seventh exemplary embodiment will be described with reference to FIG. 14. An invisible light detection system as an example of the photoelectric conversion system and a medical diagnosis system such as positron emission tomography (PET) will be described with reference to FIG. 14. Portions having the same or similar functions to those illustrated in FIGS. 1 to 13 are given the same reference numerals, and detailed descriptions thereof are omitted. The photoelectric conversion unit according to the present exemplary embodiment includes a time to digital converter (TDC) in place of the waveform shaping unit 204 and the counter circuit 205 in FIG. 2. The TDC 204 will be described below.

Figure 14:
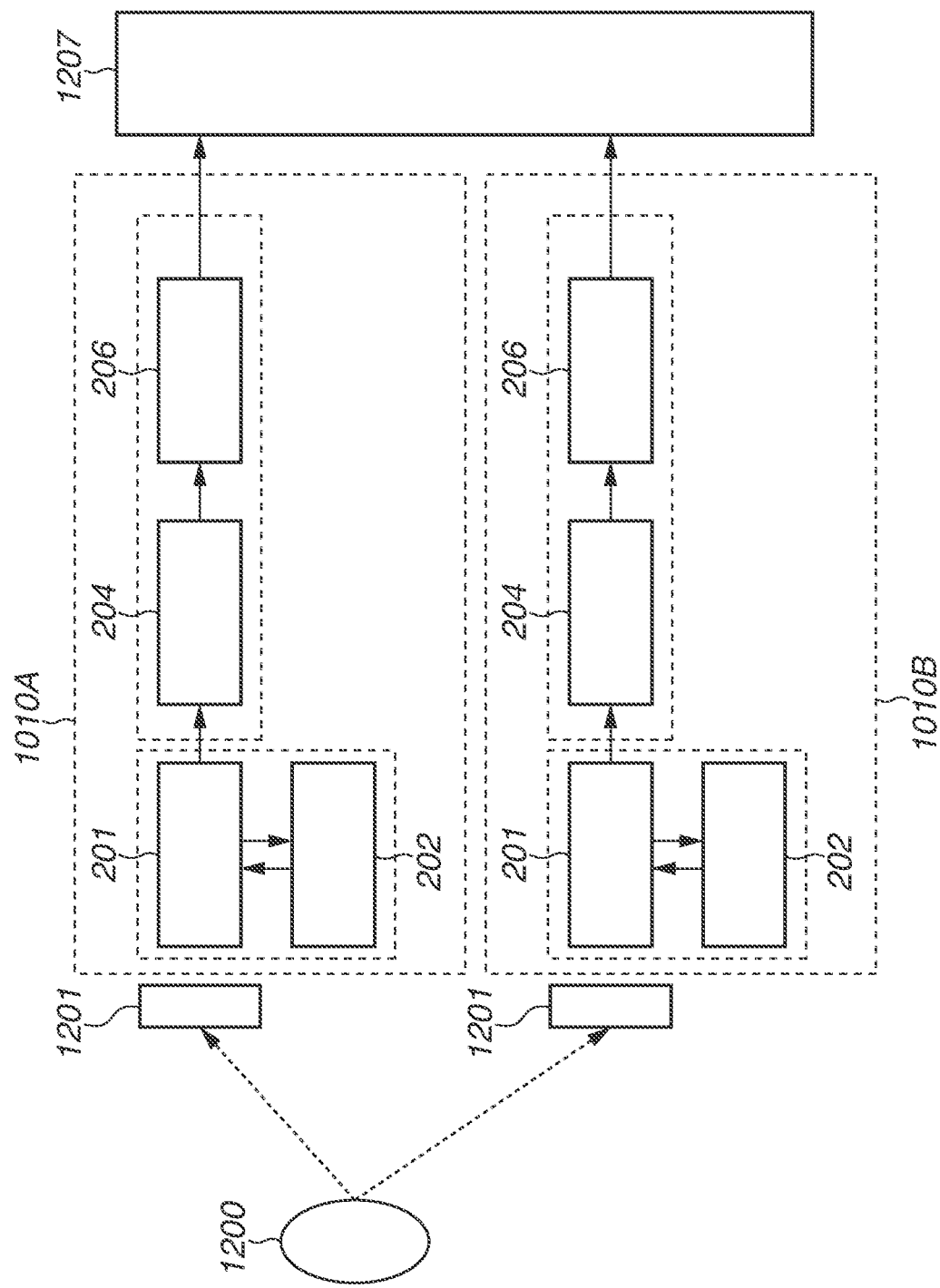
FIG. 14 is a block diagram illustrating a photoelectric conversion system according to a seventh exemplary embodiment.

FIG. 14 is a block diagram illustrating a configuration of the invisible light detection system. The invisible light detection system includes a wavelength conversion unit 1201, a data processing unit 1207, and a plurality of light detection apparatuses 1010 (1010A and 1010B). The plurality of light detection apparatuses 1010 is the photoelectric conversion apparatus according to any one of the first to sixth exemplary embodiments.

A light emitter 1200 emits light of a wavelength band of invisible light. The wavelength conversion unit 1201 receives the light of the wavelength band of invisible light that is emitted from the light emitter 1200, and emits visible light. The visible light emitted from the wavelength conversion unit 1201 enters the photoelectric conversion portion 201 and is photoelectrically converted by the photoelectric conversion portion 201, and the plurality of light detection apparatuses 1010 stores digital signals based on signals based on photoelectrically converted signal carriers on a memory 206 via a control unit 202 and the TDC 204. The plurality of light detection apparatuses 1010 may be configured as a single apparatus, or a plurality of apparatuses may be arranged, positioned, or disposed as the plurality of light detection apparatuses 1010.

The plurality of digital signals stored on the memory 206 of each of the plurality of light detection apparatuses 1010 is processed by the data processing unit 1207. In the present exemplary embodiment, the data processing unit 1207 as a signal processing unit combines a plurality of images acquired from the plurality of digital signals.

Next, a configuration of the medical diagnosis system such as PET as a specific example of the invisible light detection system will be described.

An examinee as the light emitter 1200 emits a pair of radiations from the inside of a body of the examinee. The wavelength conversion unit 1201 forms a scintillator, and if each of the pair of radiations emitted from the examinee enter the scintillator, the scintillator emits visible light. The visible light emitted from the scintillator enters the photoelectric conversion portion 201 and is photoelectrically converted by the photoelectric conversion portion 201, and each of the plurality of light detection apparatuses 1010 stores digital signal based on signal based on photoelectrically converted charge on the memory 206 via the control unit 202 and the TDC 204. In other words, the plurality of light detection apparatuses 1010 each detects the arrival time of the pair of radiation emitted from the examinee, detects the visible light emitted from the scintillator, and stores the digital signal on the memory 206.

Each of the digital signals stored on the memory 206 of each of the plurality of light detection apparatuses 1010 are processed by the data processing unit 1207. In the present exemplary embodiment, the data processing unit 1207 as a signal processing unit performs combining processing such as image reconstruction using a plurality of images acquired from the plurality of digital signals and forms an image of the inside of the body of the examinee.

An example of a photoelectric conversion system according to an eighth exemplary embodiment will be described with reference to FIG. 15. Portion having the same or similar functions as or to those illustrated in FIGS. 1 to 13 is given the same reference numerals, and detailed descriptions thereof are omitted.

Figure 15:
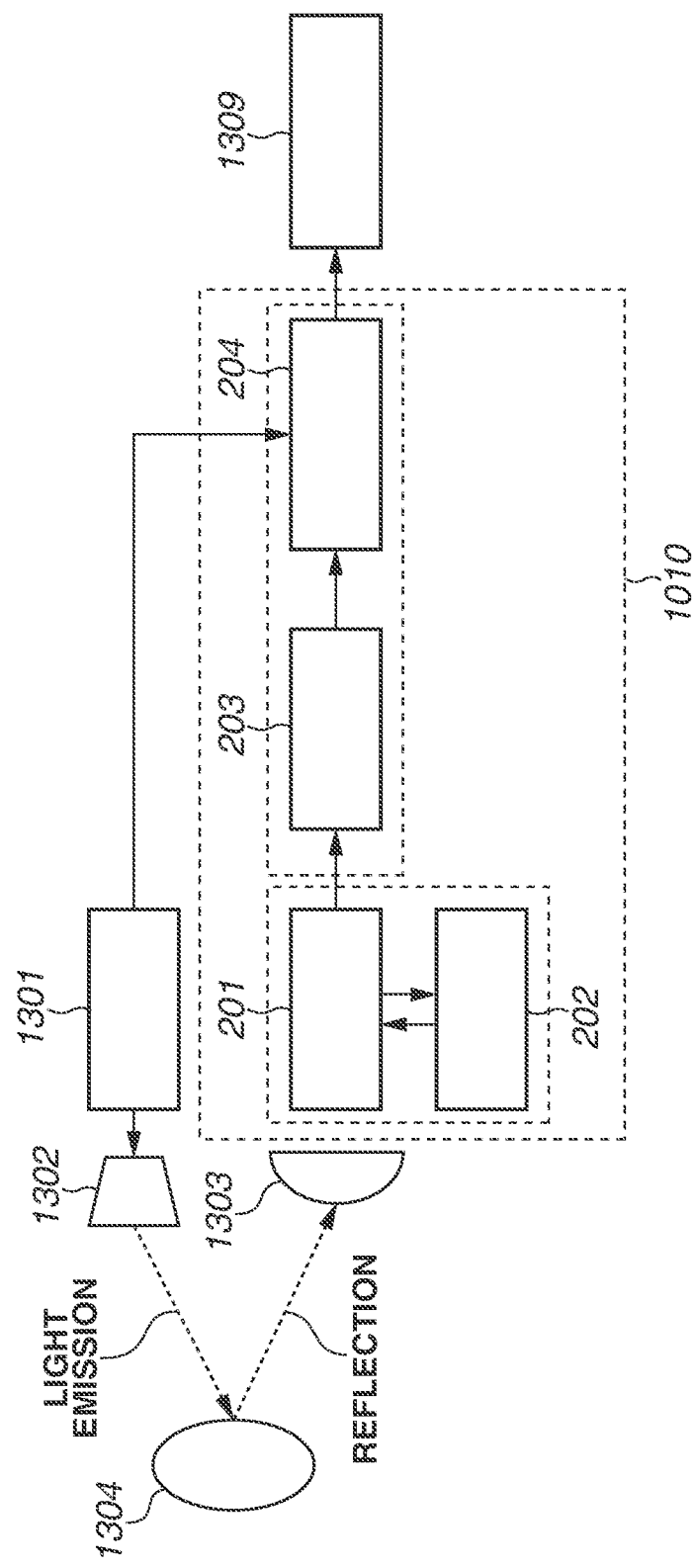
FIG. 15 is a block diagram illustrating an example of a photoelectric conversion system according to an eighth exemplary embodiment.

FIG. 15 illustrates a distance detection system as an example of the photoelectric conversion system. The photoelectric conversion portion 201 according to the present exemplary embodiment includes the TDC 204 in place of the counter circuit 205 illustrated in FIG. 2.

An example of a block diagram of the distance detection system according to the present exemplary embodiment will be described with reference to FIG. 15. The distance detection system includes a light source control unit 1301, a light emitting unit 1302, an optical member 1303, the light detection apparatus 1010, and a distance calculation unit 1309. The photoelectric conversion apparatus according to any one of the first to sixth exemplary embodiments is used as the light detection apparatus 1010.

The light source control unit 1301 controls driving of the light emitting unit 1302. When the light emitting unit 1302 receives a signal from the light source control unit 1301, the light emitting unit 1302 emits light of a short pulse (series of pulses) with respect to an image capturing direction. The light emitted by the light emitting unit 1302 is reflected by a subject 1304. The reflected light travels through the optical member 1303 and is received by the photoelectric conversion portion 201 of the light detection apparatus 1010, and a signal based on photoelectrically converted charge is input to the TDC 204 via the waveform shaping unit 203.

The TDC 204 compares the signal acquired from the light source control unit 1301 and the signal input from the waveform shaping unit 203. Then, the TDC 204 converts a time interval between the time of emission of the pulse light from the light emitting unit 1302 and the time of reception of the reflected light from the subject 1304 into a digital signal with high accuracy. A digital signal output from the TDC 204 is stored on the memory.

The distance calculation unit 1309 calculates the distance (depth) from the light detection apparatus 1010 to the subject 1304 based on the digital signals of a plurality of measurements stored on the memory 211. The distance detection system is applicable to, for example, an in-vehicle apparatus or smartphone.

Figure 16A:
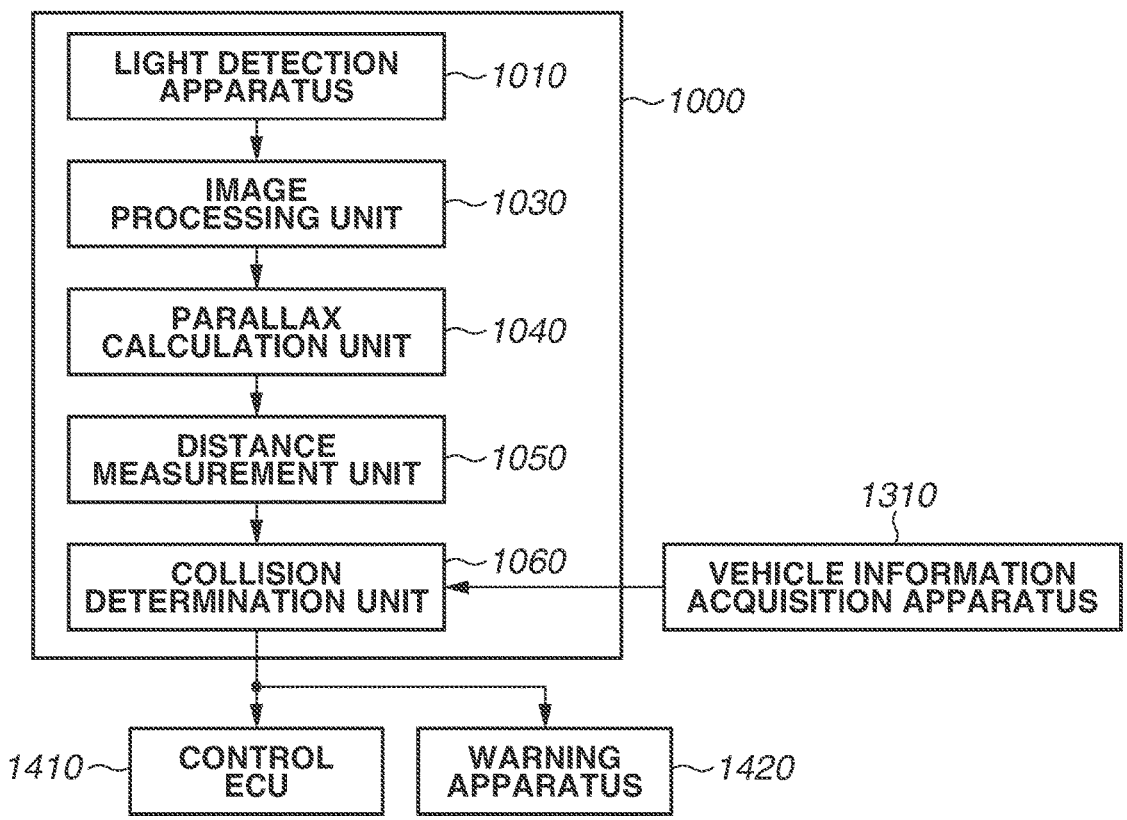
FIGS. 16A and 16B are block diagrams illustrating an example of a photoelectric conversion system according to a ninth exemplary embodiment.
Figure 16B:
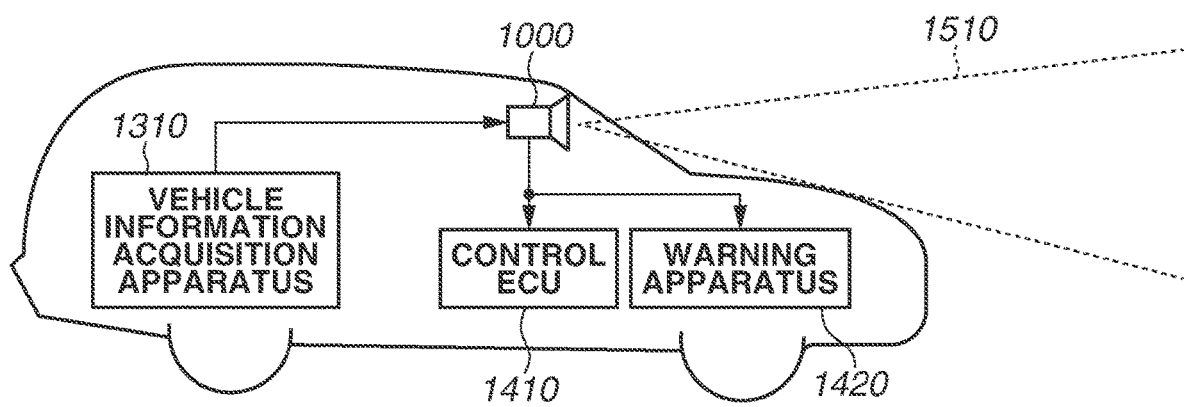

An example of a photoelectric conversion system according to a ninth exemplary embodiment will be described with reference to FIGS. 16A and 16B. In FIGS. 16A and 16B, a light detection system 1000 that relates to an in-vehicle camera is illustrated as an example of the photoelectric conversion system.

The light detection system 1000 includes an image processing unit 1030, and the image processing unit 1030 performs image processing on a plurality of digital signals acquired by the light detection apparatus 1010. The light detection apparatus 1010 is the photoelectric conversion apparatus according to any one of the first to sixth exemplary embodiments. The light detection system 1000 further includes a parallax calculation unit 1040, and the parallax calculation unit 1040 calculates a parallax (phase difference in parallax image) based on a plurality of pieces of image data acquired by the image processing unit 1030.

The light detection system 1000 further includes a distance measurement unit 1050 and a collision determination unit 1060. The distance measurement unit 1050 calculates a distance to a target object based on the calculated parallax. The collision determination unit 1060 determines whether there is a possibility of a collision based on the calculated distance. The parallax calculation unit 1040 and the distance measurement unit 1050 are an example of a distance information acquisition unit that acquires distance information about the distance to the target object. In other words, the distance information is information about at least one of the parallax, defocus amount, and distance to the target object.

The collision determination unit 1060 may use any of the distance information in determining the possibility of a collision. The distance information acquisition unit may be implemented by dedicated hardware, a software module, or a combination thereof. Further, the distance information acquisition unit may be implemented by a field programmable gate array (FPGA), an application specific integrated circuit (ASIC), or a combination thereof.

The light detection system 1000 is connected to a vehicle information acquisition apparatus 1310 and can acquire vehicle information such as a vehicle speed, yaw rate, and wheel angle. The light detection system 1000 is also connected to a control engine control unit (control ECU) 1410. The control ECU 1410 is a control apparatus that outputs a control signal for generating braking force with respect to the vehicle based on a result of the determination by the collision determination unit 1060.

The light detection system 1000 is also connected to a warning apparatus 1420. The warning apparatus 1420 provides a warning to a driver based on a result of the determination by the collision determination unit 1060. For example, in a case where the collision determination unit 1060 determines that there is a high possibility of a collision, the control ECU 1410 performs vehicle control to avoid a collision or reduce damage by applying a brake, returning an accelerator, or reducing engine output. The warning apparatus 1420 provides a warning to a user by sounding a warning such as a sound, displaying warning information on a screen of a car navigation system, or vibrating a seatbelt or steering wheel.

In the present exemplary embodiment, the light detection system 1000 captures images of a region around the vehicle, such as the front side or rear side. FIG. 16B illustrates the light detection system 1000 in a case where images of the front of the vehicle are to be captured. Further, while the control for avoiding a collision with another vehicle is described above, the present exemplary embodiment is also applicable to the control for automatic driving of following another vehicle or the control for automatic driving within a traffic lane. The light detection system is applicable to not only a vehicle such as a car but also a moving object (moving apparatus) such as a ship, aircraft, or industrial robot. Furthermore, the light detection system is applicable to not only a moving object but also a device that widely uses object recognition, such as an intelligent transport system (ITS).

With the photoelectric conversion apparatus according to any of the exemplary embodiments of the present disclosure, the power consumption is reduced.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2019-214781, filed Nov. 27, 2019, which is hereby incorporated by reference herein in its entirety.

What is claimed is:

1. A photoelectric conversion apparatus comprising:
a semiconductor substrate including a first surface and a second surface facing the first surface;
a first semiconductor region of a first conductivity type in the semiconductor substrate, the first conductivity type using, as a majority carrier, a same carrier as a signal carrier;
a second semiconductor region of a second conductivity type in the semiconductor substrate;
an embedded electrode arranged in the semiconductor substrate in a depth direction from the first surface toward the second surface; and
an insulation member arranged between the embedded electrode and the second semiconductor region, and the first semiconductor region,
wherein a deepest portion of the embedded electrode is at a position deeper than a p-n junction surface of the first semiconductor region and the second semiconductor region,
wherein a potential difference between the first semiconductor region and the second semiconductor region is a potential difference at which avalanche multiplication does not occur between the first semiconductor region and the second semiconductor region, and
wherein a potential difference between the embedded electrode and the second semiconductor region is a potential difference at which avalanche multiplication occurs between the embedded electrode and the second semiconductor region.

2. The photoelectric conversion apparatus according to claim 1, wherein the second semiconductor region is in contact with the insulation member.

3. The photoelectric conversion apparatus according to claim 1, wherein the first semiconductor region and the second semiconductor region overlap in planar view.

4. The photoelectric conversion apparatus according to claim 3, wherein the first semiconductor region and the second semiconductor region are joined to have a p-n junction.

5. The photoelectric conversion apparatus according to claim 1, wherein the deepest portion of the embedded electrode is arranged at a position deeper than the first semiconductor region.

6. The photoelectric conversion apparatus according to claim 5, wherein the first semiconductor region constitutes a portion of the first surface of the semiconductor substrate.

7. The photoelectric conversion apparatus according to claim 6,
wherein the second semiconductor region includes a first portion and a third portion having a higher impurity concentration than an impurity concentration of the first portion, and
wherein the third portion arranged in a continuous manner along the embedded electrode to a position deeper than the deepest portion of the embedded electrode.

8. The photoelectric conversion apparatus according to claim 1,
wherein the first surface includes a contact plug that feeds a potential to the embedded electrode, and
wherein the second surface is a light incidence surface.

9. The photoelectric conversion apparatus according to claim 8, wherein the second semiconductor region is in contact with the insulation member.

10. The photoelectric conversion apparatus according to claim 1,
wherein the second semiconductor region includes a first portion and a second portion having a higher impurity concentration than an impurity concentration of the first portion, and
wherein the second portion is arranged between the first surface and the first portion.

11. The photoelectric conversion apparatus according to claim 10, wherein a third semiconductor region of the first conductivity type is arranged between the second portion and the insulation member.

12. The photoelectric conversion apparatus according to claim 11, wherein the third semiconductor region has a lower impurity concentration than an impurity concentration of the first semiconductor region.

13. The photoelectric conversion apparatus according to claim 1, wherein the insulation member is arranged to surround the embedded electrode in the semiconductor substrate.

14. The photoelectric conversion apparatus according to claim 1, wherein the embedded electrode contains polysilicon.

15. The photoelectric conversion apparatus according to claim 1, wherein the embedded electrode is arranged to be surrounded by the first semiconductor region in a cross section extending through the insulation member, the embedded electrode, and the first semiconductor region.

16. The photoelectric conversion apparatus according to claim 1,
wherein a different semiconductor substrate different from the semiconductor substrate is layered on the first surface of the semiconductor substrate, and
wherein the different semiconductor substrate includes a control unit configured to control the potential to be applied to the embedded electrode.

17. A light detection system including a plurality of photoelectric conversion apparatuses according to claim 1, the light detection system comprising:
a wavelength conversion unit configured to convert light of a first wavelength band into light of a second wavelength band different from the first wavelength band; and
a signal processing unit configured to combine a plurality of images acquired from a plurality of digital signals stored on the plurality of photoelectric conversion apparatuses,
wherein the light of the second wavelength band output from the wavelength conversion unit is caused to enter the plurality of photoelectric conversion apparatuses.

18. A photoelectric conversion system including a plurality of photoelectric conversion apparatuses according to claim 1, the photoelectric conversion system comprising:
a light emitting unit configured to emit light to be detected by the plurality of photoelectric conversion apparatuses; and
a distance calculation unit configured to calculate a distance using a digital signal stored on the plurality of photoelectric conversion apparatuses.

19. A moving object comprising:
a photoelectric conversion apparatus according to claim 1;
a distance information acquisition unit configured to acquire distance information about a distance to a target object based on a signal from the photoelectric conversion apparatus; and
a control unit configured to control the moving object based on the distance information.

20. A photoelectric conversion apparatus comprising:
a semiconductor substrate including a first surface and a second surface facing the first surface;
a first semiconductor region of a first conductivity type arranged in the semiconductor substrate, first conductivity type using, as a majority carrier, a same carrier as a signal carrier;
a second semiconductor region of a second conductivity type arranged in the semiconductor substrate;
an embedded electrode arranged in the semiconductor substrate in a depth direction from the first surface toward the second surface; and
an insulation member arranged between the second semiconductor region and the embedded electrode,
wherein an avalanche multiplication region is formed between the embedded electrode and the second semiconductor region,
wherein the avalanche multiplication region is in contact with the first semiconductor region, and
wherein a potential difference between the first semiconductor region and the second semiconductor region is a potential difference at which avalanche multiplication does not occur between the first semiconductor region and the second semiconductor region.

21. The photoelectric conversion apparatus according to claim 20, wherein the second semiconductor region is in contact with the insulation member.

22. The photoelectric conversion apparatus according to claim 21, wherein the second semiconductor region is in contact with the insulation member.

23. The photoelectric conversion apparatus according to claim 20,
wherein the second semiconductor region includes a first portion and a second portion having a higher impurity concentration than an impurity concentration of the first portion, and
wherein the second portion is arranged between the first surface and the first portion.

24. The photoelectric conversion apparatus according to claim 23, wherein a third semiconductor region of the first conductivity type is arranged between the second portion and the insulation member.

25. The photoelectric conversion apparatus according to claim 20, wherein the insulation member is arranged to surround the embedded electrode in the semiconductor substrate.

26. The photoelectric conversion apparatus according to claim 20, wherein the embedded electrode contains polysilicon.

27. The photoelectric conversion apparatus according to claim 20, wherein the embedded electrode is arranged to be surrounded by the first semiconductor region in a cross section extending through the insulation member, the embedded electrode, and the first semiconductor region.

28. A photoelectric conversion system including a plurality of photoelectric conversion apparatuses according to claim 20, the photoelectric conversion system comprising:
   a light emitting unit configured to emit light to be detected by the plurality of photoelectric conversion apparatuses; and
   a distance calculation unit configured to calculate a distance using a digital signal stored on the plurality of photoelectric conversion apparatuses.

29. A moving object comprising:
   a photoelectric conversion apparatus according to claim 20;
   a distance information acquisition unit configured to acquire distance information about a distance to a target object based on a signal from the photoelectric conversion apparatus; and
   a control unit configured to control the moving object based on the distance information.

* * * * *